United States Patent [19]

Shashoua

[11] Patent Number: 5,051,448
[45] Date of Patent: Sep. 24, 1991

[54] GABA ESTERS AND GABA ANALOG ESTERS

[75] Inventor: Victor E. Shashoua, Brookline, Mass.

[73] Assignee: The McLean Hospital Corporation, Belmont, Mass.

[21] Appl. No.: 518,227

[22] Filed: May 7, 1990

Related U.S. Application Data

[63] Continuation of Ser. No. 767,903, Aug. 15, 1985, abandoned, which is a continuation-in-part of Ser. No. 519,361, Aug. 1, 1983, abandoned, and Ser. No. 640,507, Jul. 24, 1984, abandoned.

[51] Int. Cl.$^5$ ............... A61K 31/225; A61K 31/235; A61K 31/24; A61K 31/22
[52] U.S. Cl. .................. 514/547; 514/533; 514/538; 514/539; 514/540; 514/551; 260/399; 260/400; 260/401; 260/402; 260/402.5; 260/404; 260/404.5
[58] Field of Search ............ 514/533, 538, 539, 540, 514/547, 551; 260/399, 400, 401, 402, 402.5, 404, 404.5

[56] References Cited

PUBLICATIONS

Chemical Abstracts; vol. 103, (1985) #64867r; Shashoua.
Chemical Abstracts; vol. 100 (1984), #156960g; Shashoua.
Chemical Abstracts; vol. 88 (1978), #7325k; Fominova et al.
Chemical Abstracts; vol. 85 (1976), #108263g; Shmuilovich et al.
Chemical Abstracts; vol. 84 (1976), #30348w; Shmuilovich et al.
Chemical Abstracts; vol. 79 (1973), #73657k; Ostrovskaya et al.
Chemical Abstracts; vol. 68 (1968) #113074z; Berteui et al.
Jacob, J. N., Journal of Medicinal Chemistry, 1985, vol. 28, No. 1, pp. 106–110, Lipid Esters of GABA Penetrate Blood-Brain Barrier.
Hesse, G. W., et al., Neuropharmacology, vol. 24, No. 2, pp. 139–146, 1985, Cholesteryl-GABA inhibition.

Primary Examiner—Stanley J. Friedman
Assistant Examiner—Kimberly Jordan
Attorney, Agent, or Firm—Sterne, Kessler, Goldstein & Fox

[57] ABSTRACT

Ester derivatives of gamma-aminobutyric acid (GABA) and GABA analogues which cross the blood-brain barrier are disclosed, as well as methods of synthesizing and using the compounds.

The ester derivatives have the formula:

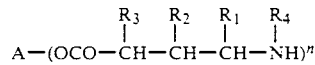

where A is a radical compound having at least one esterifiable OH group; n varies from one to the total number of esterifiable OH group contained in A; and $R_1$, $R_2$, $R_3$ and $R_4$ are hydrogen or a substituent.

73 Claims, 2 Drawing Sheets

GABA ESTERS AND GABA ANALOG ESTERS

CROSS-REFERENCE TO RELATED APPLICATIONS

This application is a continuation of application Ser. No. 06/767,903, filed Aug. 15, 1985, now abandoned, which application is a continuation-in-part of application Ser. No. 519,61, filed Aug. 1, 1983, now abandoned and Ser. No. 640,507, filed July 24, 1984, now abandoned.

BACKGROUND OF THE INVENTION

1. Field of the Invention

The present invention relates to derivatives of gamma-aminobutyric acid (GABA) and to derivatives of gamma-aminobutyric acid analogues (GABA analogues), more particularly to ester derivatives of GABA and GABA analogues which cross the blood brain barrier, as well as to methods of synthesizing and using these compounds.

2. Description of the Background Art

GABA is an amino acid which has a ubiquitous distribution in the central nervous system (CNS) and fulfills the main criteria established for the identification of a neurotransmitter:

1. GABA is synthesized and selectively released from nerve terminals,
2. the release of GABA can be induced in vitro and in vivo,
3. exogenously-applied GABA mimics the inhibitory effects elicited after neuronal stimulation,
4. pre- and post-synaptic GABA receptors have been identified, and
5. membrane transport systems and processes for determination of the neurotransmission process and for the inactivation of GABA, have been characterized.

The variation of CNS levels of GABA has been linked to certain neurological and psychiatric diseases. Low levels of GABA and of the GABA-synthesizing enzyme glutamate decarboxylase have been measured in post mortem brain tissue from patients suffering from Huntington's chorea. In Parkinson's disease, there is an imbalance between the GABA and the dopamine systems. In some brain areas of Parkinsonian patients, GABA receptor density is below normal levels. Analysis of brain samples from sites near seizure foci in epileptics revealed reduced GABA uptake capacity, probably reflecting degeneration of GABA neurons. Further, decreased GABA activity found in autopsies of schizophrenics suggests that GABA is also involved in the pathophysiology of this disease. Moreover, diseases where GABA neurons are still functioning, but at abnormally low levels, also lead to the postulation of a role for GABA in the etiology of CNS pathologies.

Under physiological conditions GABA does not significantly cross the blood-brain barrier. Thus, only at highly toxic doses was GABA shown in clinical studies to have a definite therapeutic action in epileptics, Tower, D. B., in *Nervous System Function:* 461, Roberts et al., editors, Raven Press, N.Y., (1976). Consequently, clinically useful GABA agonists or prodrugs with a capacity to cross the blood-brain barrier would have extreme therapeutic relevance for the treatment of these conditions. Such an approach requires that GABA receptors on post-synaptic sites remain intact following the degeneration of GABA neurons.

Along these lines, several attempts have been made to increase GABAergic activity in the brain by administration of GABA derivatives or analogues.

Research by Galzigna et al., *Arch. Int. Pharmacodyn.:* 235, 73 (1978), indicates that when the $NH_2$ function of GABA was blocked with either a benzoyl group, or a pivaloyl group, the resulting compounds were able to penetrate the blood-brain barrier when subcutaneously injected into rats.

Of the putative GABA mimetics which enter the brain, only muscimol has been widely examined, and even this compound enters the brain to a very limited extent, Maggi et al., *J. Neuropharmacology:* 18, 361 (1979). However, muscimol exhibits an unacceptable CNS toxicity, which prevents its wide clinical use.

Kaplan et al., *J. Med. Chem.:* 23, 702 (1980), have reported the use of derivatives where GABA is attached through an imine link (Schiff base) to a lipophilic carrier. The data show a reversal of bicuculline-induced lethality and convulsions indicating that these compounds can cross the blood-brain barrier of the rat.

Krogsgaard-Larsen, *J. Med. Chem.:* 24 (12), 1377 (1981), reviewed the use of GABA agonists, antagonists and uptake inhibitors. Baclofen and cyclic GABA structures such as muscimol and its derivatives, Kojic amine, isoguvacine, nipecotic acid and its derivatives, among others are analyzed, as well as their pharmacological activities in a variety of disorders. Of all the compounds analyzed, tetrahydroisoxazolopyridine-3-ol (THIP) penetrates the blood-brain barrier without being peripherally degraded.

Frey et al., *Neuropharmacology:* 19, 217 (1980), have shown that cetyl GABA has low anticonvulsant activity at dosages of 10–25 mg per kg when given intraperitoneally to mice and up to 100 mg per kg when given orally. The anticonvulsant effect was demonstrable only by threshold determinations, but there was substantially no protection against seizures elicited by high doses of penetrazole or by the maximal electroshock, and, in both cases, there was substantially no effect on the extensor phase of the penetrazole convulsion. In addition to this low protection against convulsions and seizures, cetyl GABA was also shown to only slightly increase GABA levels in brain, thus suggesting that cetyl GABA may not reach the brain in substantially sufficient amounts. In addition, cetyl GABA was fairly toxic when given intravenously and intraperitoneally.

Thus, a number of agents having sufficient pharmacological activity have been tested, either as GABA agonists or antagonists, or for their ability to release GABA from the CNS neurons. At best, these approaches have resulted in a trade off between improvement of transport across the blood-brain barrier, and the worsening of side effects. Accordingly, new compounds capable of crossing the blood-brain barrier are needed.

Other GABA esters are also known in the prior art.

Jones, U.S. Pat. No. 4,316,892, reported derivatives of N-enkephalin GABA to be useful as analgesics when administered orally in dosages of 0.5 to 5 mg per kg of body weight. These compounds include the free acid, lower alkyl esters, or aklylamide derivatives.

Somatostatin-GABA cyclic peptide derivatives having peripheral somatostatin-like activities have been reported by Rink et al., in U.S. Pat. No. 4,328,214. These derivatives have a strong inhibiting effect on the insulin and glucagon secretion of the pancreas, and are therefore useful in the treatment of diabetes or blood losses in the gastrointestinal tract. Cyclic peptide derivatives with marked peripheral endocrine effect and substantially devoid of CNS activities are obtained by simple modifications of the basic peptidic structure, especially by omitting individual amino acids and/or exchanging them for other amino acids.

Certain analogues of GABA are known as well, Johnson et al., "GABA-Neurotransmitters," *Alfred Benzon Symposium* 12, Munksgaard (1978), and Allan et al., *Medicinal Research Reviews*, Vol. 3, No. 2, 91–118 (1983), incorporated by reference herein. Further, Metcalf et al., "GABA-Nuerotransmitters," *Alfred Benzon Symposium* 12, Munksgaard (1978), identified two GABA analogues, gamma-acetylenic GABA and gamma-vinyl GABA, as enzyme-activated inhibitors of GABA aminotransferase. The authors suggest that by inhibiting the GABA aminotransferase, elevated brain levels of GABA could be expected, perhaps having a beneficial effect on Huntington's disease, epilepsy and schizophrenia.

Accordingly, prior to the present invention, there remained a great need for GABA and GABA analogue derivatives which could be transported across the blood-brain barrier, and which could be possibly hydrolyzed in the CNS to produce GABA and GABA analogues.

SUMMARY OF THE INVENTION

It is therefore an object of the invention to provide ester derivatives of GABA and GABA analogues which cross the blood-brain barrier.

It is also an object of this invention to provide ester derivatives of GABA and GABA analogues having a Brain Penetration Index (BPI), as defined hereinafter, greater than about 2%.

Another object of the invention is to provide ester derivatives of GABA and GABA analogues having an n-octanol/water partition coefficient ($K_{OW}$), as defined hereinafter, greater than about 1.

It is another object of the invention to provide GABA and GABA analogue esters with biological activity useful in the regulation of general locomotor activity.

It is another object of the invention to provide GABA derivatives and GABA analogue derivatives with biological activity useful in the prevention and/or treatment of seizures.

It is yet another object of the invention to provide pharmacological compositions comprising esters of GABA and esters of GABA analogues.

It is still a further object of this invention to provide a general method of synthesizing ester derivatives of GABA and ester derivatives of GABA analogues.

And yet a further object of this invention is to provide a method of regulating general motor activity in animals, including humans, and to provide a method of preventing and/or treating seizures, epilepsy, Huntington's disease, manic depression, general depression, schizophrenia and/or neuropsychiatric disorders.

These and other objects of the invention, as will hereinafter become more readily apparent, have been attained by providing:

a compound of the formula:

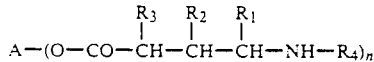

wherein $R_1$, $R_2$, and $R_3$ represent hydrogen or a substituent which may be alkyl, substituted alkyl, alkenyl, substituted alkenyl, alkynyl, substituted alkynyl, aryl, substituted aryl, hydroxy, amino, oxo, halo, or combinations of the above, with the proviso that where $R_1$, $R_2$ or $R_3$ is oxo, the corresponding hydrogen is not present, and $R_4$ is hydrogen or acyl; A represents the radical of a compound having at least one esterifiable OH group, and being substantially capable of crossing the blood-brain barrier of an animal, or pharmaceutically acceptable acid addition salts thereof; n can vary from one to the total number of esterifiable OH groups contained in A. Where $R_1$, $R_2$, $R_3$ and $R_4$ are each hydrogen, the compound is an ester of GABA. Where at least one of $R_1$, $R_2$, $R_3$ and $R_4$ is other than hydrogen, the compound is an ester of an analogue of GABA.

The objects have also been attained by providing pharmacological compositions comprising the aforementioned compounds.

A general method of synthesis for the compounds described above is also part of the present invention. This process comprises reacting GABA, or an anhydride of a GABA derivative with a compound having at least one esterifiable OH group. An esterification reaction takes place between the carboxy group of GABA and one of the hydroxy groups of the alcohol to form an ester derivative of GABA.

Further, the objects of the invention have also been attained by providing a method of promoting the uptake of GABA by the brain, and a method of treating a condition associated with abnormal GABA levels in the brain.

A method of preventing or treating seizures, epilepsy, Huntington's disease, manic depression, general depression, schizophrenia and/or neuropsychiatric disorders is also herein provided.

Other objects, advantages and features of the present invention will become apparent to those skilled in the art from the following discussion.

BRIEF DESCRIPTION OF THE DRAWINGS

FIG. 1A shows the effects of the dose of the compound on the behavior of rats and mice (n=6 per dose) and FIG. 1B shows the time course of recovery from reduced activity of the animals at a dose of 21 umol/kg (n=6 per group).

BEST MODE FOR CARRYING OUT THE INVENTION

Figure 1:
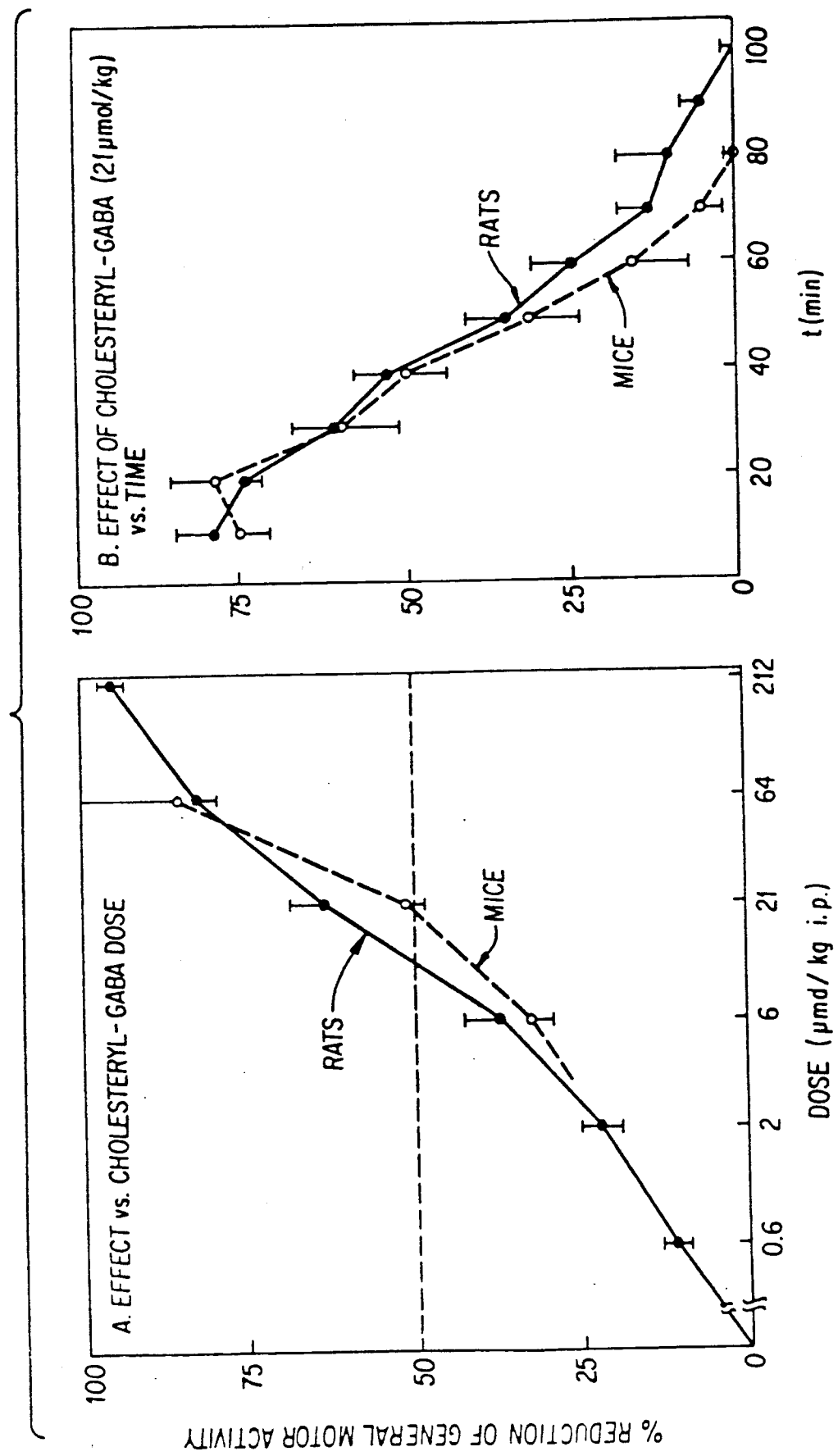
FIGS. 1A and 1B show the effects of cholesteryl-GABA on general motor activity.

By GABA and GABA analogues is intended compounds having the general formula (I):

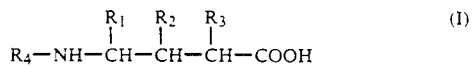

where $R_1$, $R_2$ and $R_3$ are the same or different and include, but are not limited to,
(1) hydrogen;
(2) lower alkyl groups having one to four carbon atoms;

(3) substituted lower alkyl groups having one to four carbon atoms;
(4) lower alkenyl groups having two to four carbon atoms;
(5) substituted lower alkenyl groups having two to four carbon atoms;
(6) lower alkynyl groups having two to four carbon atoms;
(7) lower substituted alkynyl groups having two to four carbon atoms;
(8) aryl groups;
(9) substituted aryl groups;
(10) hydroxy groups or protected hydroxy groups such as lower ($C_1$–$C_4$) acyl or aroyl groups;
(11) oxo groups, in which case, hydrogen is not present on the same carbon;
(12) amino groups;
(13) substituted amino groups;
(14) $R_1$ and $R_3$ together form a carbocyclic ring;
(15) $R_2$ and $R_3$ together form a carbocyclic ring.

Typical lower alkyl groups include methyl, ethyl, n-propyl, i-propyl, n-butyl, t-butyl and i-butyl. The preferred alkyl is methyl, the substitution preferably in the gamma position.

Typical substituted lower alkyl groups include alkyl groups having one to four carbon atoms and substituted with such groups as hydroxy, halo, amino, and the like. Typical substituted lower alkyl GABAs include gamma-fluoro-methyl GABA and gamma-difluoromethyl GABA.

Typical lower alkenyl groups include vinyl, allyl, and methylene, with vinyl preferred. Gamma-vinyl GABA is a preferred analogue.

Typical substituted lower alkenyl groups include the hydroxy, halo and amino substituted lower alkenyl groups.

Typical lower alkynyl groups are those lower alkynyl groups having two to four carbon atoms and include acetynyl and propargyl, with gamma-substituted lower alkynyl GABA's preferred.

Typical halo groups include fluorine, chlorine, bromine and iodine, with fluorine and chlorine preferred. Typical halo-substituted GABA's include 2- and 3-chloro-GABA and 3-fluoro-GABA.

Typical hydroxy substituted compounds include those compounds with hydroxy substituted in the alpha, beta, and gamma positions, with the alpha-hydroxy- and beta-hydroxy-GABA's preferred.

Typical aryl groups include phenyl, naphthyl, phenanthryl and anthracyl, with phenyl preferred.

Typical substituted aryl groups include aryls substituted with halo, hydroxy, amino, and the like. Halo substituted aryls are preferred, with chlorophenyl most preferred.

Typical amino groups include —$NHR_5$ where $R_5$ is hydrogen or a substituent such as hydroxy, lower alkyl, amino, or the like. Preferred amino groups are those wherein $R_5$ is hydrogen. Preferred amino-substituted GABA's are those where the amino group is substituted in the alpha position.

Typical oxo-substituted GABA's include those where the oxo group is substituted in the alpha, beta or gamma position, with beta-oxo-substituted GABA preferred.

Where $R_1$ and $R_3$ together form a carbocyclic ring, typical carbocyclic rings contain three to six carbon atoms. Typical carbocyclic rings are cyclopropane, cyclopentane, and cyclohexane, with cyclopentane the preferred carbocyclic ring. Where the carbocyclic ring contains five or six members, unsaturation in the ring is included as a part of the invention.

Where $R_2$ and $R_3$ taken together form a carbocyclic ring, typical carbocyclic rings include three to six-member carbocyclic rings, with cyclopropane preferred.

$R_4$ may be hydrogen or an acyl group where $R_4$ is acyl, preferred acyl groups include acetyl, pivaloyl, and benzoyl.

The geometric and stereoisomers of compounds having the general formula (I) are also within the scope of the present invention.

These compounds having the general formula (I) are well-known to the prior art and their synthesis within the skill of the prior art. See particularly Allan et al., supra.

By GABA esters and GABA analogue esters or esters of GABA and GABA analogues are intended compounds having the general formula (II):

$$A-(O-CO-\overset{R_3}{\underset{|}{CH}}-\overset{R_2}{\underset{|}{CH}}-\overset{R_1}{\underset{|}{CH}}-NH-R_4)_n \qquad (II)$$

where $R_1$, $R_2$, $R_3$ and $R_4$ are as described above and A represents the radical of a compound having at least one esterifiable OH group capable of crossing the blood-brain barrier of an animal, and n can vary from 1 to the total number of esterifiable OH groups contained in A. Moreover, pharmaceutically acceptable acid addition salts of the former compounds, are also a part of the present invention.

The compounds from which A is derived may be endogenous or exogenous to mammals. However, the extent to which these compounds have free access to the brain from the blood flow makes them useful for the preparation of the present GABA esters and GABA analogue esters. These compounds comprise a broad range of lipophilicities. While for some, crossing the blood-brain barrier is accomplished through an active transport system, other compounds are taken up by the brain passively by diffusion. The compounds of use in the present invention are those which when present in the blood flow can cross the blood-brain barrier to a substantial extent.

The criterion used herein for measuring the extent to which a compound, from which the radical A is derived, crosses the blood-brain barrier is based on the uptake of this compound by the brain relative to its uptake by the liver. The liver was chosen as a reference since it is an organ which has no barrier to diffusible molecules present in the blood. Measurements of the quantity of a compound present in brain and liver at 5 minutes after a subcutaneous (s.c.) injection were used to calculate a Brain Penetration Index (BPI), with the equation:

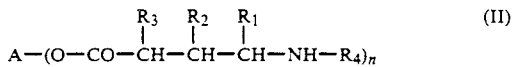

$$BPI = \frac{(brain)}{(liver)} \times 100$$

This is the amount of the compound present per gram of brain tissue as a percent of the amount per gram of liver tissue.

This procedure has the advantage that even for a sparingly soluble lipid ester, which tends to remain largely at the site of the injection and slowly diffuse into the circulation, its level in the liver will reflect the amount available rather than the initial dose injected.

Some of the preferred compounds from which the radical A is derived are those having a BPI of between about 2 and 500%.

Some of the most preferred compounds have a BPI of between about 3 and 300%; and still more preferred are those compounds having a BPI of between 25 and 200%.

A may be selected from the group consisting of compounds derived from carbohydrates, saturated aliphatic alcohols having more than one OH substituent, unsaturated aliphatic alcohols and their derivatives containing one or more heteroatoms, saturated and unsaturated cyclic alcohols, heterocyclic alcohols, aromatic alcohols and their derivatives containing one or more heteroatoms, and glycerides which are unesterified or esterified with saturated and unsaturated aliphatic fatty acids. Also included is dihydroxyacetone.

The ester derivatives of GABA and GABA analogues may be in the form of the free amines (on the N-terminus) or acid addition salts thereof. Acid addition salts may be, e.g., hydrohalic acid salts, for example salts of HBr, HF, HCl; also included are acetate, ascorbate, and tartarate salts.

Preferred are those GABA and GABA analogue esters having a Brain Penetration Index (BPI), as defined hereinbefore, greater than about 2%. Among this group, preferred are those compounds which have a BPI greater than about 3%; but most preferred yet, are those GABA and GABA analogue esters having a BPI greater than about 25%.

Also preferred among the esters of GABA and GABA analogues are those wherein A is the radical of a carbohydrate having a carbon chain of $C_3$–$C_{20}$ carbon atoms, their O-acetyl derivatives, their O-methyl derivatives, their deoxy-D-derivatives, their amino derivatives and their acid derivatives.

Among the most preferred carbohydrates are those having a carbon chain of 3 to 7 carbon atoms.

Some of the most preferred, are carbohydrates of the formula:

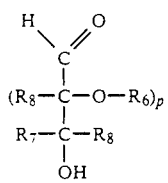

wherein:
(1) p is 1 to 18,
(2) $R_6$, $R_7$ and $R_8$ may be the same or different and represent:
  (a) H;
  (b) OH, except that $R_7$ and $R_8$ cannot be OH;
  (c) branched or unbranched amino of the formula $(CH_2)_nNH_2$, wherein n is 1 to 15;
  (d) branched or unbranched hydrazino of the formula $(CH_2)_nNHNH_2$, wherein n is as defined above;
  (e) haloalkyl of the formula $(CH_2)_nCX_mH_{3-m)}$, wherein n is as defined above and m is 1 to 3;
  (f) alkyl of 1 to 15 carbon atoms;
  (g) alkenyl of 1 to 15 carbon atoms;
  (h) alkynyl of 1 to 15 carbon atoms; or
  (i) $(CH_2)_nOPO_3H_2$, wherein n is as defined above; and in addition (3) $R_7$ and $R_8$ may be the same or different and represent haloalkyl of the formula $CX_mH_{3-m)}$ wherein m and X are as defined above;
(4) $R_6$ represents acetyl.

Representative GABA and GABA analogue esters of the present invention are those wherein A is a carbohydrate derived from D-glyceraldehyde, D-erythrose, D-threose, D-ribose, D-arabinose, D-xylose, D-allose, D-glucose, D-mannose, D-gulose, D-idose, D-galactose, D-talose, dihydroxy acetone, D-erythrulose, D-ribulose, D-xylulose, D-psikose, D-fructose, D-sorbose, their O-acetyl derivatives, their O-methyl derivatives, their corresponding deoxy-D-derivatives, their corresponding amino derivatives; and their corresponding acid derivatives.

Also preferred among the ester derivatives of GABA and GABA analogues are those wherein A is a radical or a branched or unbranched saturated aliphatic alcohol having a carbon chain of 18 to 40 carbon atoms. Some of the most preferred are those having an even number of carbon atoms, and those having a carbon chain containing 20 to 26 carbon atoms.

Preferred among the GABA and GABA analogue esters are also those wherein A is a radical derived from a branched or unbranched saturated aliphatic alcohol having a carbon chain with 2 to 40 carbon atoms. Some of the most preferred are those having an even number of carbon atoms, and those having a carbon chain containing 20 to 26 carbon atoms.

Among the most preferred alcohols are those having multiple hydroxyl substituents.

Representative ester derivatives of the present invention, wherein A represents a radical of a branched or unbranched saturated aliphatic polyalcohol, are those derived from glycerol, n-butanol, isobutanol, sec-butanol, 1,2,3,4-tetrahydroxybutanol, n-pentanol, isopentanol, 1,2,3,4-tetrahydroxypentanol, n-hexanol, n-heptanol, n-octanol, n-decanol, n-dodecanol, n-tetradecanol, n-octadecanol, n-eicosanol, and n-tetracosanol.

Also preferred are the GABA and GABA analogue esters wherein A is the radical of an aliphatic alcohol having one or more points of unsaturation of a carbon chain consisting of 3 to 40 carbon atoms. Among these, preferred are those with a carbon chain having an even number of carbon atoms. Another group of preferred alcohols is alkynyl alcohols.

Another group of preferred compounds is that having aliphatic alcohols with one or more points of unsaturation and a carbon chain of 4 to 30 carbon atoms. Among the most preferred unsaturated alcohols are those having a carbon chain of 8 to 20 carbon atoms.

Some of the most preferred alcohols are the alkenyl and alkynyl alcohols with multiple points of unsaturation, and among these the most preferred ones are those with an even number of carbon atoms in the carbon chain.

Representative GABA and GABA analogue esters of the present invention, wherein A represents a radical of a branched or unbranched aliphatic alcohol having at least one point of unsaturation, are those derived from allyl alcohol, crotyl alcohol, methylvinylcarbonol, palmitolyl alcohol, oleic alcohol, linoleic alcohol, linolenic alcohol, arachidonic alcohol, lactobacillic alcohol, cerebronic alcohol, their alkyl derivatives of 1 to 10 carbons, their corresponding hydroxyl derivatives, their corresponding halo derivatives having F, Cl, Br or I, their corresponding amino derivatives, and their corresponding acid derivatives.

Preferred among the GABA and GABA analogue esters, are also those wherein A is the radical of a saturated or unsaturated cyclic alcohol with one or more points of unsaturation. Also preferred are those cyclic alcohols having one or more carbon rings with a maximum of 18 ring carbon atoms. Also preferred are those wherein one or more of the carbon rings is derived from alkenyl or alkynyl alcohols with multiple unsaturation points.

Some of the most preferred cyclic alcohols are those having 5 to 14 carbon ring atoms. Another group of preferred cyclic alcohols is that having 6 to 10 carbon atoms.

Most preferred among the cyclic alcohols are those having an even number of carbon atoms. Some of the most preferred cyclic alcohols are those having multiple hydroxyl substituents.

Representative GABA and GABA analogue esters of the present invention, wherein A represents the radical of a branched or unbranched, saturated or unsaturated cyclic alcohol, are those derived from cyclopentanol, cyclohexanol, cycloheptanol, cyclooctanol, cyclodecanol, cyclododecanol, cyclotetradecanol, cyclohexadecanol, cyclooctadecanol, inositol, their derivatives having multiple hydroxyl substituents, their O-acetyl derivatives, their O-methyl derivatives, their amine derivatives, and their halogenated derivatives.

Also representative GABA and GABA analogue esters of the present invention, wherein A represents a radical of a branched or unbranched, saturated or unsaturated cyclic alcohol, containing one or more unsaturated rings, are those derived from dexamethasone having the formula:

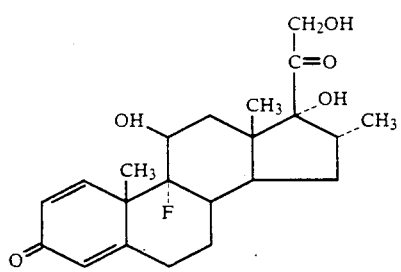

Also preferred among the GABA and GABA analogue esters of cyclic alcohols are those wherein A is the radical of an alcohol containing one or more aromatic carbon rings. Among some of the most preferred compounds are those having one unsaturated carbon ring and containing a maximum of 18 carbon ring atoms.

Also preferred are the alcohols selected from the group consisting of the aliphatic and alicyclic alkyl, alkenyl and alkynyl alcohols having one or more points of unsaturation and the aromatic alcohols of the formula:

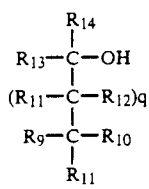

wherein:
(1) q is 1 to 38;
(2) $R_9$, $R_{10}$, $R_{11}$, $R_{12}$, $R_{13}$ and $R_{14}$ may be the same or different, and represent:
 (a) H, with the proviso that at least one is different from H;
 (b) OH, except that $R_{13}$ and $R_{14}$ are not OH;
 (c) branched or unbranched groups of the formula $(CH_2)_nNH_2$, wherein n is 1 to 15;
 (d) branched or unbranched alkyl groups of 1 to 15 carbon atoms;
 (e) branched or unbranched hydrazino groups of the formula $(CH_2)_nNHNH_2$, wherein n is as defined above;
 (f) branched or unbranched haloalkyl groups of the formula $(CH_2)_nCX_mH_{3-m}$, wherein
  X represents F, Cl, Br, or I,
  n is defined as above, and
  m is 1 to 3;
 (g) branched or unbranched alkenyl of 2 to 15 carbon atoms;
 (h) branched or unbranched alkynyl of 2 to 15 carbon atoms;
 (i) acetyl;
 (j) their O-acetyl derivatives;
 (k) their O-methyl derivatives; and,
if there is at least one carbon ring,
(3) $R_{10}$ and $R_{12}$ may be a cyclic structure containing one or more carbon rings.

Also preferred among the GABA and GABA analogue esters are those where A is the radical of an alcohol having one or more heteroatoms. Most preferred heteroalcohols are those having a carbon chain of 2 to 40 carbon atoms. Among the most preferred alcohols are those having a carbon chain with 6 to 30 carbon atoms. Among these, most preferred are those alcohols having a carbon chain with 10 to 26 carbon atoms.

Also preferred are those alcohols containing one or more nitrogen, sulfur or oxygen atoms, or a combination thereof.

Also preferred are those heteroalcohols having one or more carbon rings. Among these, the most preferred ones are those having 1 or more points of unsaturation in the hetero ring.

Still another group of preferred heteroalcohols are those having one or more aromatic rings.

Representative GABA and GABA analogue derivatives of the present invention, wherein A represents a radical of a branched or unbranched aliphatic or cyclic alcohol having one or more heterocyclic atoms, are those derived from ethanolamine, choline, serine, O-aminoacylglycerol, their alkyl derivatives of 1 to 15 carbon atoms, their O-methyl derivatives of 1 to 15 carbon atoms, their O-acyl derivatives of 1 to 15 carbon atoms, and the corresponding haloacid addition salts.

Some of the preferred compounds of the present invention are those wherein A represents a radical of a glycerol esterified with from 1-2 radicals of carboxylic acids having a carbon chain with 2 to 60 carbon atoms.

Among these, some of the most preferred are those compounds having carboxylicacids with an even number of carbon atoms. Another group of preferred carboxylic acids are fatty acids having a carbon chain of 6 to 40 carbon atoms and some of the most preferred among them are fatty acids with 10 to 30 chain carbon atoms. Another group of preferred compounds are those where the fatty acids have at least one point of unsaturation. And yet another group of preferred GABA and GABA analogue esters are those where the fatty acids have multiple points of unsaturation.

Further representative GABA and GABA analogue esters of the present invention, wherein A represents a radical of a glycerol esterified with from 1 to 2 radicals of fatty acids, which may be the same or different, are those derived from lauric acid, myristic acid, palmitic acid, stearic acid, arachidic acid, palmitoleic acid, oleic acid, linoleic acid, linolenic acid, arachidonic acid, cerebronic acid, cardiolypin, their O-acetyl derivatives, their O-methyl derivatives; and their amino derivatives.

Among the most preferred ester derivatives of GABA of this invention are butyl-GABA, butyl-gamma-vinyl GABA, linolenoyl-GABA, linolenoyl-gamma-vinyl GABA, dexamethasone-GABA, dexamethasone-gamma-vinyl GABA, glyceryl-GABA, glyceryl-gamma-vinyl GABA, cholesterol-GABA, cholesterol-gamma-vinyl GABA, inositol-monoGABA, inositol-gamma-vinyl GABA, inositol-diGABA, inositol-di(-gamma-vinyl GABA), inositol-triGABA, inositol-tri(-gamma-vinyl GABA), diGABA-linolenoyl-glyceride, divinyl GABA-linolenoyl-glyceride, GABA-dilinolenoyl-glyceride, vinyl GABA-dilinolenoyl-glyceride and their acid addition salts.

Among the broad objectives of the present invention has been to develop a general method for the exogenous regulation of GABA and GABA analogue levels in brain. Given that GABA and GABA analogues are not taken up by the CNS in sufficient amounts, a replacement therapy approach was conceived based on the rationale of attaching GABA and GABA analogue to other compounds capable of penetrating the blood-brain barrier.

Thus, GABA, a substantially hydrophilic neurotransmitter, or a GABA analogue, is coupled to the radical A of a compound such as glucose, inositol and cholesterol, among others to be transported into the CNS. As in the case of the compound from which the radical A is derived, the criterion used herein for selecting the GABA or GABA analogue derivatives of the present invention is based on the extent of their uptake by the brain. Preferred GABA and GABA analogue derivatives are those which substantially penerate the brain, as measured by the BPI hereinbefore defined.

While the BPI value for GABA is about 1% (see Example 1), a compound for which there is substantially no blood-brain barrier has a BPI of about 100%, or equal uptake per gram of brain or liver. Compounds with BPI values substantially greater than 100% preferably accumulate in the brain and are also useful.

Some of the preferred compounds of this invention are those having a BPI of between about 2–500%. Some of the most preferred GABA and GABA analogue esters are those having a BPI of between about 3–300%, or 25 to 200%.

After crossing the blood-brain barrier, the compounds of the present invention act as agonists, partial agonists, antagonists and inhibitors of CNS-mediated activity. These GABA and GABA analogue esters act at the pre- and post-synaptic neurons, at membrane sites and at the different GABA receptor sites, as well as acting, in some cases, as inhibitors of the enzymes which catabolize GABA.

Additionally, since the attachment of these compounds to GABA and GABA analogues is through an ester bond, these derivatives act as prodrugs which may be hydrolyzed in situ providing a means to increase GABA and GABA analogue levels in the CNS. Given the different characteristics of the groups attached to GABA and GABA analogues, the rate of hydrolysis will be different for different GABA and GABA analogue ester derivatives. Thus, shorter and longer acting compounds, having GABAergic activities, are produced.

Some of the GABA and GABA analogue derivatives preferentially locate in specific parts of the brain tissues. Thus, compounds with different radicals have different biological activities which are also different from those of GABA or the GABA analogue itself. Such compounds are useful as dissecting tools of the neuroanatomy of the different GABA receptors in brain and in the treatment of different conditions. The latter effect is a consequence of the fact that while a GABA receptor present in one area of the brain causes, e.g., a decrease in locomotor activity, the same receptor present in another circuit in a different area of the brain causes, e.g., enhanced locomotor activity in an animal.

Since a significant proportion of the brain is composed of extracellular space and some of the present compounds are substantially water-soluble they are thus capable of acting at receptors located therein. Other compounds which are more lipid-soluble are capable of interacting with receptors located in the lipid areas of the brain. These compounds show a biological activity related to the receptors located in more lipidic tissues.

Some of the preferred compounds accumulate preferentially in the CNS after administration and, thus, their presence in brain tissues increases with time. The storage of lipid-soluble compounds in lipophilic-tissues is well known. The more lipophilic GABA esters are stored in the brain and are slowly released from their lipid tissue storage. Due to the similarity of some of the compounds to natural components of membrane lipids, some of the GABA and GABA analogue derivatives can also become associated with brain membrane lipid bilayers. The storage of these GABA or GABA analogue esters provides a reservoir for the release of GABA or GABA analogue by hydrolysis by the esterases present in the cerebrospinal fluid (CSF) and brain membrane.

Additionally, some of the GABA and GABA analogue compounds show a multiple-phase response. This is the case, e.g., of monolinolenoyl-diGABA glyceride, which has a stimulating activity at low doses, while behaving as a sedative at high doses.

The criterion used herein for selecting those GABA and GABA analogue esters having biological activity when administered to an animal is based on their differential lipid-water solubilities. A Partition Coefficient was defined by the equation:

$$K_{OW} = \frac{\text{(n-Octanol)}}{\text{(H}_2\text{O)}}$$

representing the amount of the ester taken up per ml of n-octanol relative to the amount of the same compound taken up per ml of water.

Compounds having significantly low values of $K_{OW}$ have not yet been shown to have biological activity. GABA itself has a $K_{OW}$ of about 0.004 and is inactive when administered to an animal. A compound having a $K_{OW}$ of about 1 will be as soluble in octanol as in water.

Typical GABA and GABA analogue esters have a $K_{OW}$ of between about 0.1–10,000. Preferred compounds are those having a $K_{OW}$ of between about 0.5–5,000. A further group of preferred compounds is that having a $K_{OW}$ of between about 0.5–1,000. Some of the most preferred GABA and GABA analogue esters have a $K_{OW}$ of between 0.5–600.

Compounds of the invention can be synthesized by any general method of ester synthesis now known or discovered in the future. However, as has been previously mentioned, this invention also encompasses a general method of synthesis of ester derivatives of GABA and GABA analogues. This reaction is shown schematically, hereinafter, as Schemes I, II, III and IV.

Some of the compounds can be synthesized by simple esterification of GABA or a GABA analogue and the corresponding alcohol in the presence of a strong acid, as is the case for the butyl ester of GABA or GABA analogue shown in Scheme I.

SCHEME I

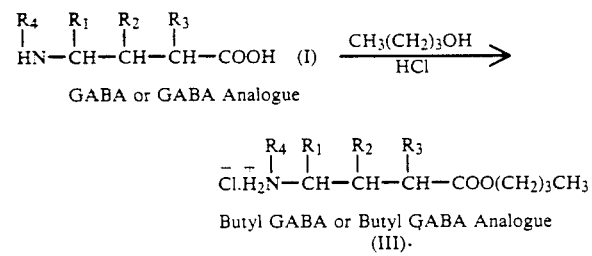

Butyl GABA or Butyl GABA Analogue
(III).

The preferred strategy for the synthesis of compounds having several OH groups, such as glyceryl derivatives and polyalcohols such as inositol or different carbohydrates, includes the protection of the various OH groups not to be esterified, by forming an acetonide derivative as shown in Scheme II, below. When reacting a hydroxy GABA analogue, it may also be necessary to protect the hydroxy group or groups. Appropriate protecting groups include lower ($C_1$–$C_4$) acyl or lower substituted acyl, e.g.

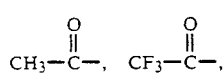

or aroyl, e.g.

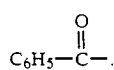

SCHEME II

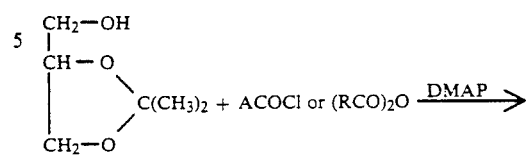

Glycerol Acetonide (20)
[DMAP: 4-dimethylaminopyridine]

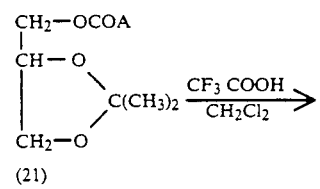

(21)

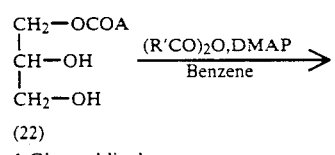

(22)
1-Glyceryl-linolenoate

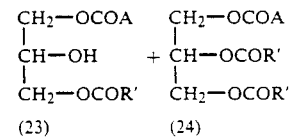

(23)    (24)

A: $CH_3(CH_2CH=CH)_3(CH_2)_7-$

R′: $(CH_3)_3COCON-CH-CH-CH-$ with $R_4\ R_1\ R_2\ R_3$

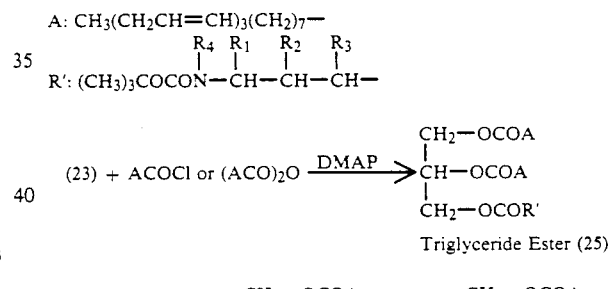

Triglyceride Ester (25)

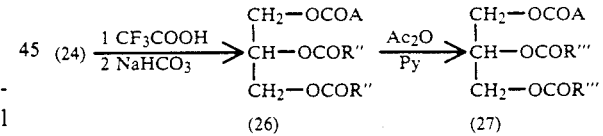

(26)    (27)

R″: $-CH-CH-CH-NH$ with $R_3\ R_2\ R_1\ R_4$    R‴: $-CH-CH-CH-NCOCH_3$ with $R_3\ R_2\ R_1\ R_4$

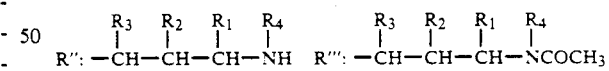

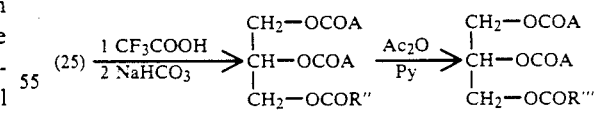

This general scheme also applies to the synthesis of mono, di, tri, and multiple GABA and GABA analogue derivatives of compounds such as inositol or different carbohydrates.

In the case of the glyceryl derivatives, two of the hydroxyl groups of glycerol can be protected by forming an acetonide, then the remaining hydroxyl group can be esterified with the symmetrical anhydride of a fatty acid in the presence of, for instance 4-dimethylaminopyridine, in a dry organic solvent to give the corresponding ester plus one mole of the fatty acid. This product after purification, e.g., chromatography on silica gel, can be next treated with a strong acid, e.g., trifluoroacetic acid, at 0°-5° C. in an organic solvent, e.g., methylene chloride, to give the diol ester. This compound can be separated again, e.g., on a silica gel column, from the unconverted starting material.

Further treatment of the mono ester of glycerol, with a GABA or GABA analogue anhydride having the amino terminus protected, e.g., with a t-butoxycarbonyl radical, in the presence of, for example, 4-dimethylaminopyridine, and an organic solvent, e.g., benzene, gives a mixture of compounds having one and two GABA or GABA analogue ester bonds in addition to the fatty acid ester bond. Different molar equivalent amounts of the GABA or GABA analogue anhydride reagent can be used to increase the amount obtained of one or the other. These mono and di GABA or GABA analogue ester derivatives can be separated from the starting materials, e.g., by chromatography on silica gel.

Further treatment of the diester derivative having a free hydroxyl group with the anhydride of chloride derivative of a fatty acid in the presence of, e.g., 4-dimethylaminopyridine, yields the corresponding triester with only one GABA or GABA analogue. All three mono, di and tri esters thus obtained can be converted to their free amino derivatives by treatment with trifluoroacetic acid at 0°-5° C. under a nitrogen atmosphere to remove the protecting groups. The trifluoroacetate salts formed after this step can be converted to the free amines by extraction of chloroform solutions of these compounds with dilute aqueous sodium bicarbonate. The free amines and the intermediates are fairly stable when stored in chloroform solution below 0° C.

The mono-GABA or mono-GABA analogue ester of glycerol can be synthesized by reacting the mono-acetonide of glycerol with N-carbobenzoxy-GABA anhydride or N-carbobenzoxy-GABA analogue anhydride to obtain the corresponding ester. This product can be converted to glyceryl GABA or glyceryl GABA analogue by hydrogenolysis and treatment with trifluoroacetic acid. This route is shown in general in Scheme III.

As is well understood by those with ordinary skill in the art, similar blocking techniques may be utilized to protect reactive substituents along the carbon chain of the GABA analogue precursors as well, for example, where $R_1$, $R_2$ or $R_3$ is a hydroxy group.

SCHEME III

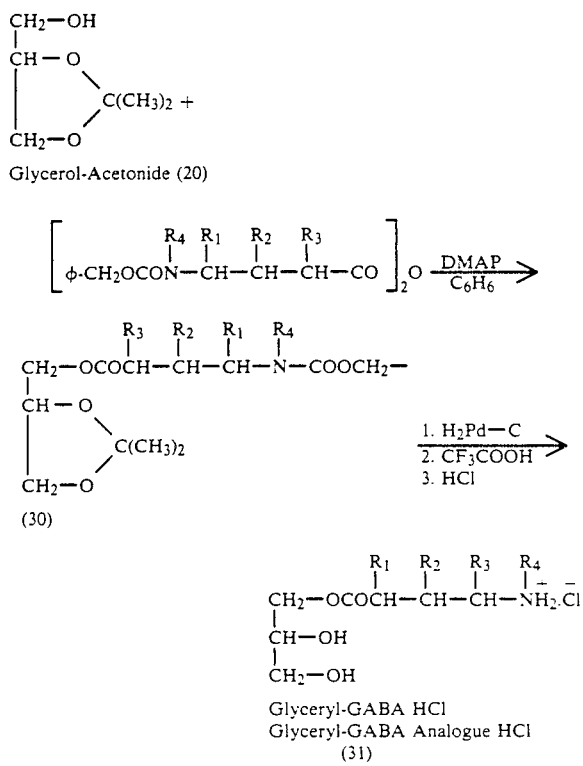

Glyceryl-GABA HCl
Glyceryl-GABA Analogue HCl
(31)

The various GABA and GABA analogue esters shown in Schemes II and III can also be synthesized on a microscale as radioactive derivatives using $^{14}$C-labeled t-BOC-GABA anhydride or t-BOC-GABA analogue anhydride with all the radioactivity present in the GABA or GABA analogue moiety of the molecule.

Ester derivatives of GABA and GABA analogue, with compounds such as long-chain alcohols, cholesterol, and the like, and dexamethazone-like radicals, can be synthesized according to the reactions in Scheme IV.

SCHEME IV

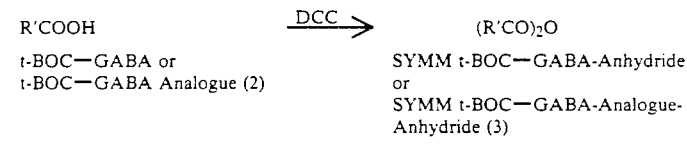

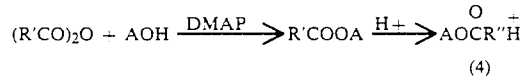

| A | COMPOUND |
|---|---|
| $-CH_2(CH_2)_7(CH=CH-CH_2)_3CH_3$ | Linolenyl-GABA or Linolenyl-GABA Analogue (5) |

SCHEME IV

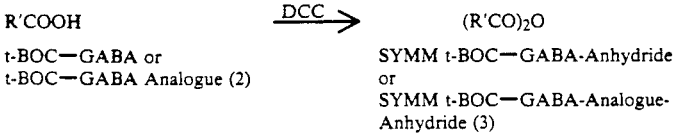

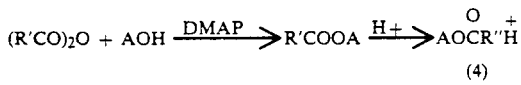

| A | COMPOUND |
|---|---|
| 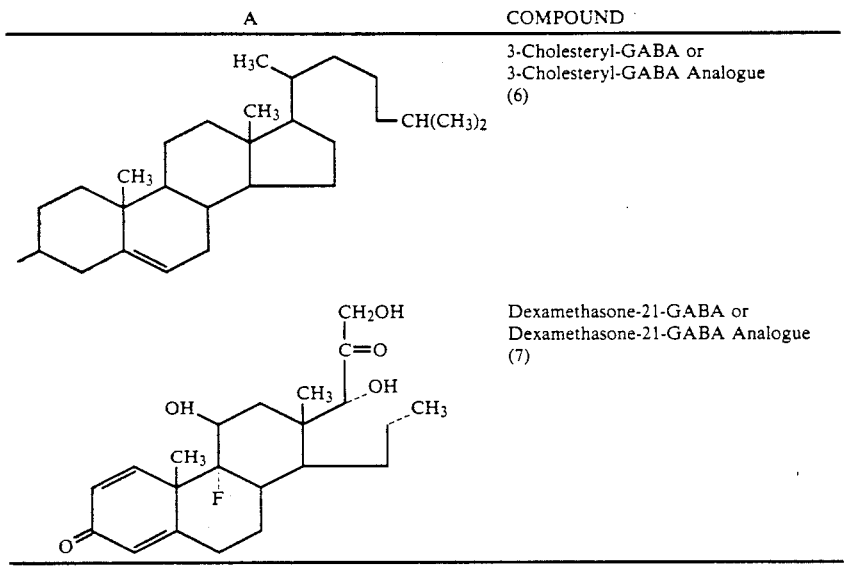 | 3-Cholesteryl-GABA or 3-Cholesteryl-GABA Analogue (6) |
| | Dexamethasone-21-GABA or Dexamethasone-21-GABA Analogue (7) |

DCC = dicyclohexyl carbodiimide
DMAP = 4-diemthylaminopyridine

The amino group of GABA or GABA analogue can be first protected, e.g., by formation of its t-butoxycarbonyl derivative (t-BOC-GABA or t-BOC-GABA analogue), by reaction with t-BOC-ON reagent. This product can be converted to the symmetrical anhydride by using, e.g., dicyclohexylcarbodiimide (DCC). Different alcohols can then be esterified by reaction with the GABA or GABA analogue anhydride to yield the GABA or GABA analogue ester products. After treatment of these compounds with a strong acid, e.g., trifluoroacetic acid, to remove the t-BOC group, the desired GABA or GABA analogue esters are obtained.

Similar methods on a microscale can be used to prepare these esters as radioactive derivatives with all the radioactivity present as $^{14}C$ in the GABA or GABA analogue moiety of the molecules. The IR and NMR spectra and elemental analysis of the compounds can be used to check consistency with their proposed structures.

Additional steps, such as those leading to further purification of the compounds, are also possible.

When the compounds of the invention are used to promote the uptake of GABA or GABA analogue by the brain, they are administered to an animal, e.g., a human, in need of higher brain levels of GABA, in an amount sufficient to promote the crossing of the blood-brain barrier of said animal by the compound.

When the ester derivatives of GABA or GABA analogue of the present invention are used for treating a condition associated with abnormal GABA in the brain, they are administered to an animal, e.g., a human, susceptible to said condition in an amount sufficient to normalize said GABA levels.

When the ester derivatives of the present invention are used for treating a condition such as epilepsy, Huntington's disease, manic depression, general depression, schizophrenia and neuropsychiatric disorders, they are administered to an animal, e.g., a human, in need of such a treatment, in an amount sufficient to treat said condition.

When the present compounds are used to regulate general locomotor activity, they are administered to an animal, e.g., a human, in need of such regulation in an amount sufficient to regulate such activity.

When the ester derivatives of this invention are used for preventing or treating a condition associated with seizures, they are administered to an animal, e.g., a human, susceptible to seizures, in an amount sufficient to prevent or treat said seizures.

Administration may be by any method which allows the active compound to reach the bloodstream and penetrate through the blood-brain barrier. Typical methods include oral, rectal, peritoneal and topical administration of the compounds. When the compounds are administered orally, the composition can be in the form of dragees, tablets, syrups or ampules. When the compounds are administered rectally, the composition can be in the form of a suppository. In addition, when the compounds of the invention are to be administered by topical application, they can be in the form of a pomade or a gel.

The compounds of the invention can be prepared in pharmaceutical preparations containing the compounds themselves and a pharmaceutically acceptable carrier. The pharmaceutically acceptable carrier may be solid or liquid. Examples of liquid carriers include water, an aqueous solution of non-toxic salts, such as sterile physiological solutions of saline, or aqueous solutions containing organic solvents, such as ethanol. Also suitable are emulsions, such as oil-in-water emulsions. Solid carriers include both nutritive carriers, such as sucrose or gelatin, and non-nutritive carriers, such as cellulose, alpha-cyclodextrin, or talc. Slow-release capsules and other protective means are particularly suitable for the oral administration of the present compounds due to the protection afforded against hydrolysis in the gastrointestinal tract. Preferred are those capsules which permit the compounds to bypass the stomach. When the present compounds are to be administered peritoneally, they can be administered by subcutaneous, intramuscular or intravenous injections.

Amounts of ester derivatives of GABA or GABA analogue useful for promoting the uptake of GABA or GABA analogue by the brain may vary from individual to individual, and can be determined by experimentation as is well understood by those skilled in the pharmaceutical arts. For intravenous injection, amounts in the range of about 1–1000 umol/kg body weight are preferred. Also a preferred range is between about 1–500 umol/kg. Especially preferred are amounts in the range of 1–100 umol/kg body weight. Compounds of the invention have been found to be effective on mammals (mice) within this range.

Generally, compounds are more active when administered intravenously than by the other preferred routes. For oral, topical, or rectal administration, as well as for the subcutaneous, or intramuscular injection of the compounds, amounts in the range of about 1–2000 umol/kg body weight, are preferred. Also a preferred range is between about 1–1000 umol/kg body weight. Especially preferred are amounts in the range of about 1–200 umol/kg.

The above disclosure generally describes the present invention. A more complete understanding can be obtained by reference to the following specific examples which are provided herein for purposes of illustration only and are not intended to be limiting unless otherwise specified.

EXAMPLES

Synthesis of Ester Derivatives of GABA

Melting points were determined on a hot stage apparatus and are uncorrected. IR spectra were obtained in a Perkin-Elmer Infracord spectrophotometer and are reported in cm$^{-1}$; NMR spectra were determined in a CFT 20 using tetramethylsilane as an internal reference. Elemental analyses for C, H and N were carried out by Midwest Micro Labs Ltd., Ind.; all compounds analyzed within ±0.4% of their theoretical values. Thin-layer chromatographic (TLC) determinations were carried out on silica gel-coated plastic TLC sheets from Eastman Kodak using the following solvent systems (in vols):

(A) chloroform, acetic acid (9:1);
(B) chloroform, methanol (9:3);
(C) propanol, acetic acid, water (4:1:1);
(D) chloroform, methanol, acetic acid (90:30:3);
(E) chloroform, methanol, acetic acid (18:6:1);
(F) ethyl acetate, acetic acid, ethanol (9:1:1);
(G) benzene, acetone (9:1);
(H) ethylacetate, hexane (1:1).

EXAMPLE 1

Synthesis of the Butyl Ester of GABA

The butyl ester of GABA was prepared in very high yield by direct esterification of GABA with n-butanol by the method shown in Scheme I in the specification.

A solution of 100 mg of $\gamma$-aminobutyric acid in 30 ml anhydrous n-butanol (dried over calcium hydride and distilled) was saturated with anhydrous HCl gas and sealed in a glass ampule. The mixture was heated over a steam bath for 16 hr and then evaporated to dryness to yield a white solid which was crystallized from an ethanol/ether mixture. The yield obtained was 92% based on GABA. The compound had the following characteristics:

Melting point: 72° C.
TLC in solvent A: $R_F$ 0.44 (single spot)
IR (Neat): 3550, 1730

The radioactive n-butyl ester of GABA was prepared as above using 4 mg of GABA, 50 uCi of (U, $^{14}$C)GABA (New England Nuclear, Boston, Mass.) and 3 ml of anhydrous butanol as starting materials. The radioactive product was obtained in 82% yield with a specific activity of 186 uCi/mM. On TLC plates all of the radioactivity (99%) was found to be associated with a single spot which co-migrated with the unlabeled ester at $R_F$ 0.44 in solvent A. After hydrolysis of the ester with alkali, all the radioactivity was transferred to the position of GABA on TLC plates. The yield for this reaction, and the activity of the $^3$H butyl ester of GABA are shown in Table I, hereinafter.

EXAMPLE 2

Synthesis of the 9,12,15-Octadecatrienyl Alcohol (Linolenoyl), Cholesteryl, and Dexamethasone Esters of GABA These ester derivatives of GABA were synthesized by esterification of the corresponding alcohol with the symmetrical anhydride of t-butoxycarbonyl-GABA according to Scheme IV in the specification.

The t-butoxycarbonyl-aminobutyric acid (t-BOC-GABA, Compound 2)

This compound was prepared by the reaction of GABA with a t-BOC derivative (2-(t-butoxycarbonyl oxiimino)-2-phenylacetonitrile). The BOC-ON compound was obtained in 96% yield according to published methods. The product had a melting point of 52°–54° in agreement with literature values and migrated as a single spot on TLC plates. $R_F$ values were 0.84 and 0.71 in solvents E and F, respectively. ($^{14}$C)t-BOC-GABA was also prepared from 30 mg quantities GABA and 100 uCi uniformly labeled $^{14}$C-GABA (New England Nuclear).

Symmetrical t-BOC-GABA Anhydride (Compound 3)

A cold solution (0° C.) of 558 mg dicyclohexyl carbodiimide in 8 ml of dry methylene chloride was added to a cold solution of t-BOC-GABA 1.05 g in 7 ml of dry methylene chloride. An immediate precipitate of dicyclohexylurea was formed. The mixture was then stirred for an additional 2 hr at room temperature and then filtered to remove the urea derivative. The filtrate was evaporated on a rotary evaporator. The solid product obtained was redissolved in 20 ml of anhydrous ethyl acetate and kept overnight at 4° C. to allow further precipitation of any remaining dicyclohexylurea. The resulting solution was then filtered, concentrated to 8 ml in vacuo, and dry petroleum ether was added to precipitate a white compound. This compound was isolated by filtration, washed with a mixture of ethyl acetate/petroleum ether (¼, vols), dried in vacuo over $P_2O_5$ and then crystallized from the solvent mixture to yield 915 mg of the anhydride (87%). The compound had the following characteristics:

Melting point: 160° C.,
TLC in solvent F: $R_F$ 0.74
IR (Nujol): 3480, 3400, 1810, 1730, 1680
Anal. (C,H,N): $C_{18}H_{32}N_2O_7$ The radioactive anhydride was synthesized as above with an 84% yield, using 15 mg of $^{14}C$-labeled t-BOC-GABA as a starting material. The product had a specific activity of 2 mCi/mM and an $R_F$ value identical to the unlabeled compound.

t-BOC-GABA Cholesterol Ester (Compound 8)

A solution of 1.63 g of t-BOC-GABA anhydride in 25 ml of tetrahydrofuran (distilled just before use from calcium hydride) was added to a solution of 1.35 g of cholesterol and dry tetrahydrofuran, followed by 427 mg of dry 4-dimethylaminopyridine. The mixture was stirred under nitrogen for 48 hr at room temperature and then evaporated to dryness to give a waxy solid. The product was dissolved in 7 ml of ethyl acetate, washed (3×) with 15 ml of 5% (w/v) sodium bicarbonate and then (3×) with 15 ml of distilled water. The ethyl acetate solution was separated and dried over anhydrous sodium sulfate, filtered and then evaporated to dryness. The product was recrystallized from acetone/water to yield 1.95 g of the t-BOC-GABA cholesterol ester having the following characteristics:

Melting point: 122.5° C.
TLC: $R_F$ 0.98 and 0.52 in solvents D and G, respectively The $^{14}C$-labeled compound was synthesized as above using 300 mg of cholesterol as a starting material.
Yield: 83%
Specific activity: 13.6 uCi/mM
IR: 3450, 1730, 1690, 1700
NMR ($CDCl_3$) δ5.35 (bm, 1H), 4.55 (m, 2H), 3.15 (m, 2H), 2.10-2.40 (m, 4H), 1.45 (s, 9H)
Anal: $C_{36}H_{61}NO_4$ (C, H, N).

(3-Cholesteryl)-gamma-Aminobutyrate (Compound 6)

A solution of γ-t-BOC amino-butyrylester of cholesterol (100 mg, 175 umol) in 0.53 ml of 4M HCl in dioxane and 2.0 ml of dry dioxane was stirred at room temperature for 70 min. The solution was concentrated in vacuo at room temperature, and the white solid thus obtained was washed repeatedly with ethylacetate and dried under vacuum over $P_2O_5$ to give 50 mg of the 3-cholesteryl-GABA ester Compound 6 (Yield 60%). The compound had the following characteristics:

TLC in solvent E: $R_F$=0.38 and in solvent B: $R_F$=0.33

Since the amine hydrochloride was very hydroscopic, good IR and NMR spectra could be obtained only by making the N-acetyl derivative by acetylation with acetic anhydride in pyridine. The N-acetyl derivative had the following characteristics:

IR (Neat): 3350, 1720, 1630

NMR in ($CDCl_3$): δ 5.3 (bm, 1H), 3.2 (m, 2H), 2.3-1.0 (bm), 1.96 (s, 3H), 1.26 (s, 3H), 0.9 (s, 3H)
Anal.: $C_{32}H_{54}NO_2$ Cl.$H_2$) (C, H, N)

9,12,15-Octadecatrienyl-4-(t-butoxycarbonyl)aminobutyrate (linolenoyl ester of t-BOC-GABA) (Compound 9)

To a solution of linolenyl alcohol (285 mg, 1.05 mmol) in 35 ml of benzene under an atmosphere of nitrogen was added t-BOC-GABA anhydride (480 mg, 1.24 mmol) and 4-dimethylaminopyridine (150 mg, 1.23 mmol). The mixture was stirred at room temperature for 4 hr. The solution was then washed with 5% sodium bicarbonate, ice-cold 0.1N HCl solution and finally with ice-cold water. The organic layer was then dried over anhydrous sodium sulfate and concentrated to yield 370 mg (76%) of the ester (Compound 9). The compound had the following characteristics:

TLC in solvent H: $R_F$=0.74
IR (Neat): 3500, 1720, 1160
NMR in ($CDCl_3$): 5.36 δ(m, 6H), 4.55 (bm, 1H), 4.06 (t(J 6.5 Hz), 2H), 3.15 (m, 2H), 2.8 (m, 4H), 2.29 (m, 2H), 2.0-1.3 (bm, 18H), 1.43 (s, 9H), 0.97 (t(J=7.5 Hz), 3H)

A similar procedure was used to prepare the $^{14}C$-labeled derivative using ($^{14}C$)t-BOC-GABA anhydride and unlabeled cholesterol (10 mg) with a yield of 70%.

TLC in Solvent H: $R_F$=0.73

Linolenoyl Ester of γ-aminobutyric Acid (Compound 5)

A solution of t-BOC-GABA ester of linolenyl alcohol (330 mg, 0.74 mmol) in 20 ml of methylene chloride was cooled with ice under nitrogen atmosphere. Trifluoroacetic acid (0.5 ml) was added to the solution, and the mixture was stirred at 0° C. for 1 hr, and at room temperature for an additional 2 hr. The solution was concentrated in aspirator vacuum, and the residue was taken up in 20 ml of chloroform and washed with 5% (w/v) sodium bicarbonate solution and with water. The chloroform layer was dried over anhydrous magnesium sulfate and was concentrated under vacuum to yield a light yellow liquid, 200 mg (0.58 mmol) (yield 78%). Because of its hygroscopic properties, the linolenoyl ester of GABA (Compound 5), was converted to its N-acetyl derivative with acetic anhydride in pyridine prior to its characterization and elemental analysis. The characteristics of the compound were as follows:

TLC in solvent B: $R_F$=0.43
IR (Neat): 3300, 1730, 1650, 1550
NMR ($CDCl_3$): 5.36 (m, 6H), 4.05 (t(J=4.8 Hz), 2H), 32.8 (m, 2H), 2.8 (m, 4H), 2.35 (t(J=6.6 Hz), 2H), 2.0-1.30 (bm, 18H), 1.95 (s, 3H), 1.59 (s, 3H), 0.97 (t(J=7.5 Hz), 3H)
Anal.: ($C_{24}H_{41}NO_3$) C,H,N.

The radioactive derivative was prepared from $^{14}C$-labeled t-BOC-GABA linolenoyl ester (7 mg) as above. The specific activity of the final compound was 120 uCi/mol.

9-Fluoro-11 β,17-dihydroxy-21-(N-gamma-t-BOC aminobutyroxy)-16 α-methyl pregna-1,4-diene-3,20-dione(21-(N-gamma-t-BOC-aminobutyroyl) dexamethasone) (Compound 11)

A solution of dexamethasone (Sigma) (120 mg, 0.31 mmol), t-BOC-GABA anhydride (144 mg, 0.37 mmol) and 4-dimethylaminopyridine (45 mg, 0.37 mmol) in 20 ml of dry methylene chloride was stirred at room temperature for 70 min. The solution was washed serially with 5% (w/v) sodium bicarbonate solution, 0.1N HCl and brine. The organic layer was dried over anhydrous Na₂SO₄ and was concentrated in vacuo to obtain 0.164 g (0.28 mmol) of the ester (Compound 11) with a yield of 92%. The characteristics of the ethyl acetate derivative were as follows:

M.P.: 117°-9° C.

TLC: $R_F=0.74$ (ethyl acetate), $R_F=0.38$ (dexamethasone)

IR (CHCl₃): 3500, 1710, 1660

NMR (CDCl₃): δ 7.27 (d(J=10.5 Hz) 1H) 6.37-6.1 (m, 2H), 4.89 (s, 2H), 4.75-4.05 (m, 2H), 3.19 (m, 2H) 2.48 (m, 2H), 1.63 (s, 3H), 1.54 (s, 2H), 1.44 (s, 9H), 1.05 (s, 3H), 0.91 (d(J=7.3 Hz), 3H)

Anal (C₃₁H₄₄FNO₈) C,H,N

The radioactive derivative was prepared as above using ¹⁴C-labeled t-BOC-GABA anhydride and 10 mg of dexamethasone.

Dexamethasone-21-gamma-aminobutyrate (Compound 7)

A solution of dexamethasone-21-N-gamma-t-BOC aminobutyrate (400 mg, 0.69 mmol) and trifluoroacetic acid, 0.2 ml in 20 ml of methylene chloride was stirred at room temperature for 1 hr, and the mixture was concentrated in vacuo. The residue was taken up in 9 ml of 0.1N HCl and was lyophilized. The crude product was purified on a silica gel column (20×1 cm) eluting with CHCl₃, CH₃OH (40:10 vols). The eluate was evaporated to dryness and the residue was taken up in 10 ml water and was freeze-dried to obtain the dexamethasone GABA ester product (Compound 7) as the trifluoroacetate monohydrate, a fluffy solid, 207 mg (yield 58%). The characteristics of the compound were as follows:

TLC in solvent B: $R_F=0.76$, in solvent C: $R_F=0.52$

M.P.: 185°-88° C.

IR (Neat): 3500, 1720, 1670, 1650, 1620

NMR (acetone D₆): δ 7.26 (m, 1H), 6.0-6.24 m, 2H), 4.99 (d(J=1.9 Hz), 2H), 4.1-4.7 (bm, 2H), 3.84 (m, 2H), 3.30 (s, 3H), 2.40-2.86 (m, 14H), 1.61 (s, 3H), 0.98 (m, 3H)

Anal: (trifluoroacetate) (C₂₈H₃₇F₄NO₈ H₂O) C,H,N.

The ¹⁴C-labeled dexamethasone-21-γ-aminobutyrate was obtained from the t-BOC derivatives as above using 6 mg of starting material. The characteristics of the radiolabeled compound were as follows:

Yield: 75%

Specific activity: 34 uCi/mmol.

The yields for the overall synthesis of some of these compounds labeled in the GABA radical are shown in Table I, hereinafter. The results of the elemental analysis of compounds 2, 4, 5, 6, 9, 11 and 12 are shown in Table II also hereinafter.

TABLE I

| SYNTHESIS OF ESTER DERIVATIVES OF GABA | | |
|---|---|---|
| GABA DERIVATIVE | YIELD | SPECIFIC ACTIVITY[a] uCi/mM |
| glyceryl-GABA | 40% | 645 |
| dexamethasone-GABA | 28% | 34 |
| inositol-mono GABA | 82% | 4.2 |
| 3-glucosyl-GABA | 87% | 228 |
| butyl-GABA | 92% | 3680[b] |

TABLE I-continued

| SYNTHESIS OF ESTER DERIVATIVES OF GABA | | |
|---|---|---|
| GABA DERIVATIVE | YIELD | SPECIFIC ACTIVITY[a] uCi/mM |
| linolenoyl-GABA | 70% | 120 |
| glyceride linolenoyl diGABA | 75% | 139 |
| di linolenoyl monoGABA-glyceride | 60% | 41 |
| inositol-diGABA | 35% | 7.1 |
| cholesteryl-GABA | 86% | 13.6 |

[a]¹⁴C labeled in the GABA radical of molecule
[b]³H labeled in the GABA radical of the molecule

TABLE II

| ELEMENTAL ANALYSIS RESULTS | | | | | | |
|---|---|---|---|---|---|---|
| | THEORETICAL | | | OBSERVED | | |
| COMPOUND | % C | % H | % N | % C | % H | % N |
| SCHEME IV | | | | | | |
| 3 | 55.65 | 8.30 | 7.21 | 55.61 | 8.37 | 7.18 |
| 6 | 70.78 | 10.65 | 2.66 | 70.72 | 10.28 | 2.82 |
| 7 | 55.17 | 6.40 | 2.30 | 55.51 | 5.94 | 2.26 |
| 8 | 75.61 | 10.75 | 2.45 | 75.75 | 10.83 | 2.42 |
| 10 | 73.60 | 10.46 | 3.58 | 73.15 | 10.34 | 3.59 |
| 11 | 64.42 | 7.62 | 2.42 | 64.03 | 7.68 | 2.37 |
| SCHEMES II AND III | | | | | | |
| 2 | 73.47 | 10.20 | | 73.29 | 10.37 | |
| 4 | 67.04 | 9.50 | 2.61 | 66.61 | 9.77 | 2.83 |
| 5 | 64.82 | 9.14 | 3.88 | 64.56 | 9.34 | 4.06 |
| 6 | 72.22 | 9.98 | 1.76 | 71.69 | 10.37 | 1.75 |
| 9 | 61.64 | 7.12 | 3.99 | 61.30 | 7.29 | 3.82 |
| 11 | 65.35 | 8.91 | 4.62 | 65.60 | 9.24 | 4.46 |
| 12* | 71.33 | 9.91 | 1.85 | 71.18 | 10.47 | 1.91 |

*Was hygroscopic and highly unstable, and the values represent one mole of water of hydration.

BIOLOGICAL STUDIES WITH THE COMPOUNDS OF EXAMPLES 1 AND 2

Comparative Brain/Liver Uptake of GABA

The uptake of a ¹⁴C-labeled compound into brain was compared with the uptake into liver of the same animal. Table III summarizes the results of the application of this method to ¹⁴C-labeled GABA. The data indicate that the BPI values $(mean \pm S.E.M. = 0.96 \pm 0.09\%)$ were independent of the route of administration (i.p., s.c., or i.v.) of the compound and the dose (30-380 umol/kg)

TABLE III

| UPTAKE OF (¹⁴C)GABA BY MOUSE TISSUES | | | | |
|---|---|---|---|---|
| DOSE (mol/kg) | INJECTION ROUTE | (BRAIN) (nmol/g) | (LIVER) (nmol/g) | BPI (5 min) (%) |
| 30 | i.v. | 0.04 | 4.2 | 0.95 |
| 60 | i.p. | 0.23 | 29 | 0.80 |
| 120 | i.p. | 0.45 | 46 | 1.00 |
| 160 | i.p. | 0.66 | 71 | 0.93 |
| 210 | i.p. | 0.83 | 83 | 1.00 |
| 270 | s.c. | 1.03 | 104 | 1.00 |
| 380 | s.c. | 1.81 | 165 | 1.10 |

Mean ± S.E.M.: 0.96 ± 0.09
BPI: (Brain/Liver) × 100

Comparative Brain/Liver Uptake of the GABA Esters

Table IV gives the results obtained for the brain uptake of the GABA esters.

TABLE IV

TIME COURSE OF UPTAKE OF ($^{14}$C) LABELED GABA ESTERS

| GABA ESTER | DOSE (mol/kg) | TIME (Min) | (BRAIN) (nmol/g) | (LIVER) (nmol/g) | BPI (%) |
|---|---|---|---|---|---|
| n-butanol- | 380 | 5 | 19.2 ± 0.3 | 26.0 ± 1.6 | 74 ± 3.4 |
| GABA (1) | 380 | 60 | 14.4 | 13.7 | 105 |
| 1-Linolenoyl- | 260 | 5 | 3.5 ± 0.4 | 141.7 ± 8 | 2 ± 0.6 |
| GABA (5) | 260 | 15 | 11.0 | 220.8 | 5 |
|  | 260 | 45 | 24.9 | 33.3 | 75 |
| Cholesteryl- | 50 | 5 | 0.17 ± 0.03 | 0.69 ± .08 | 25 ± 7 |
| GABA (6) | 50 | 15 | 0.67 | 1.19 | 56 |
|  | 50 | 60 | 0.79 | 0.92 | 86 |
|  | 50 | 180 | 0.60 | 1.89 | 32 |
| Dexametha- | 70 | 5 | 8.7 ± 1 | 10.8 ± 2 | 81 ± 20 |
| sone GABA (7) | 70 | 15 | 21.5 | 29.0 | 74 |

BPI = Brain Penetration Index = (Brain)/(Liver) × 100. ($^{14}$C) labeled compounds were injected s.c. into mice in 0.5 ml of 25% (vols) propylene glycol in water. The data for the 5-min BPI measurements are mean ± S.E.M. (n = 3 animals).

The 5-min PBI data indicate that the uptake of the dexamethasone, n-butyl, cholesteryl and 1-linolenoyl esters are, respectively, increased by a factor of 81-, 74-, 25- and 2-fold over GABA. Apparently, the enhanced lipid solubility of the molecules facilitated their uptake into the brain. Results at longer times than 5 min indicate that accumulation of radioactivity in brain persisted for 45-60 min post-injection for the linolenoyl and cholesteryl esters, whereas the concentrations in the liver were more variable over time. These results indicate that the GABA esters can enter the CNS and may remain there for at least 1 hr or 2 hr. TLC analysis of brain homogenates at 1 hr after administration indicates that about 70% of the labeled cholesteryl GABA and 4% of the butyl GABA ester are present as intact molecules. The remaining radioactivity migrated in the GABA region of the chromatogram.

All determinations were carried out at 5 min after injection. The volumes of the injected doses into mice (body weight, 18-24 g) for the i.v., i.p., and s.c. doses were 0.15, 0.3 and 0.5 ml, respectively. The measured concentrations in brain and liver represent the actual amounts of GABA found by thin-layer chromatographic (TLC) analysis of the tissue homogenates. Each tissue was homogenized in 8 ml of pyridine in a glass homogenizer. The precipitated material was removed by centrifugation for 10 min at 12,000×g and the supernatant was evaporated to dryness under $N_2$ and analyzed by TLC in Solvent A. This procedure insured that only labeled GABA, and not its metabolites, was being measured. The mean BPI for labeled GABA was 0.96±0.09% (n=7) and was apparently not dependent on the route of injection and the dose (between 30 and 380 umol/kg).

Each labeled test compound was injected as a solution in 0.5 ml of saline (Compound 7) or in 25% propylene glycol in water (Compounds 1, 5, 6) subcutaneously (s.c.) into young adult Balb/c mice (18-24. g body weight). After 5 min (or longer) animals were sacrificed and the brain and liver removed, weighed and homogenized respectively in 8 ml and 10 ml of brain protein solvent (1% (w/v) sodium dodecyl sulfate in 6 M urea and 19 mM EDTA, pH 7.4, 0.03M phosphate). Aliquots (0.5 ml) of the homogenates were mixed with 10 ml of Aquasol 2 (New England Nuclear) and counted in a Beckman liquid scintillation counter. The total uptake of each compound per g brain and liver tissue was calculated. The proportion of uptake into brain as compared to liver (100%) of the same animal was designated as the Brain Penetration Index (BPI), expressed as a percentage typically at 5 min after injection.

PHARMACOLOGICAL STUDIES WITH THE COMPOUNDS OF EXAMPLES 1 AND 2

Two test methods were used to evaluate the neuropharmacological activities of the GABA esters.

(1) General locomotor activity of mice

The effect of intraperitoneal (i.p.) injections of test compounds on the general motor activity of mice during a 60-min period was determined in a Stoelting electronic activity monitor. Dose-response curves were obtained from which the half-maximally effective values were calculated and the results are shown in Table V.

TABLE V

PHARMACOLOGICAL TESTING OF GABA ESTERS GENERAL MOTOR ACTIVITY DATA

| COMPOUND | DOSE (umol/kg, i.p.) | GENERAL MOTOR ACTIVITY |
|---|---|---|
| GABA | 1942 | 100 ± 15 |
| n-Butyl-GABA | 307 | 89 ± 9 |
|  | 654 | 83 ± 15 |
| 1-Linolenoyl-GABA | 34 | 90 ± 2 |
|  | 103 | 74 ± 3* |
| Cholesteryl-GABA | 6 | 67 ± 3* |
|  | 21 | 49 ± 4** |
|  | 65 | 15 ± 14** |
| Dexamethasone-GABA | 27 | 94 ± 10 |

Cumulative activity scores over 60 min post-injection of drug expressed as mean percentage of appropriate vehicle control for each drug. (x ± S.E.M., n = 6)
*p < 0.01
**p < 0.001 by t-test GABA itself had no significant effect at a dose of 1.94 mmol/kg, i.p., or when 500 ug of the compound was administered intracisternally directly into the cerebrospinal fluid. This observation is similar to previous experiments in which systemically injected GABA doses of up to 1 g/kg (9.7 mmol/kg) had little effect on motor activity in rats.

The dexamethasone, butyl and linolenyl esters were not active by this behavioral test, but the cholesteryl ester was active in reducing the general activity of test mice as shown in Table V.

Dose-response measurements in rats and mice are shown in FIG. 1. The data indicate that motor activity was reduced by 50% at i.p. injected doses of 8 and 17 umol/kg, respectively, in the two species. The amount of the compound present in the mouse brain at 5 min after a dose of 50 umol/kg, considerably larger than the ED$_{50}$ of 17 umol/kg, was only 0.17 nmol/g (Table IV) and so indicates that cholesteryl-GABA is a highly active compound in mice. This result is comparable to the effects of direct administration of muscimol (1.75 nmol/g) and baclofen (0.25 nmol/g) by cannula into the nucleus accumbens of rat brain.

The compounds were dissolved in 25% (vols.) propylene glycol in water and injected i.p. into Balb/c mice (18-24 g). Dose-response measurements were obtained for 6 animals per dose or time point. Activity was monitored for 60 min using a Stoelting Electronic Activity Monitor (EAM) apparatus to assess the general motor activity of the animals. The dose at which a compound reduced such spontaneous motor activity by 50% in comparison to the control (vehicle-injected and uninjected) animals was used as a measure of pharmacological activity.

Anticonvulsant Activity in Mice

In a second behavioral test, the ability of a substance to prevent or delay the onset of bicuculline-induced epileptic seizures was measured. There were no significant effects at 1 or 6 hr. At 24 hr after i.p. injection of the cholesteryl derivative at a dose of 30 mg/kg (64 umol/kg), the onset of seizures was delayed by 30% after an acute i.p. injection of bicuculline at 0.3 mg/kg. In contrast, the linolenyl ester of GABA had the surprising property of accelerating the seizure onset time by 70% at a dose of 50 mg/kg, even though it had an insignificant effect on the general motor activity of mice (Table V). The dexamethasone and butyl esters had no effect.

Since these changes were detected at 24 hr after administration of the GABA esters, it is not known whether they are due to the properties of the intact ester itself, to free GABA, or to other metabolites. Nevertheless, these results suggest that the cholesteryl ester of GABA had a central depressant effect but had only a slight anticonvulsant property in the test used.

The compounds were also injected i.p. at 1, 6 and 24 hr before the administration of bicuculline (0.3 mg/kg) s.c. The latency to the onset of generalized tonic-clonic epileptic seizures and the protection against the lethality of bicuculline were measured and evaluated as a percent of the data for vehicle-injected controls. No significant changes were obtained at the 1 hr and 6 hr time points. At the 24 hr time, however, some compounds delayed while others accelerated the onset of seizures.

EXAMPLE 3

Synthesis of Glyceryl Esters of GABA Further Substituted by Linolenoyl Radicals

Two of the hydroxyl groups of glycerol were first protected by forming a glycerol acetonide:

1-Linolenoyl-2-,3-0-isopropylidine glycerol a) Using Linolenoic anhydride

A solution of glycerol acetonide 470 mg, 3.55 umol), linolenic anhydride (from Sigma Chemical Co., St. Louis) (1.902 g, 3.5 mmol) and 4-dimethylaminopyridine (460 mg, 3.8 umol) in dry benzene was stirred at room temperature under N$_2$ atmosphere for 8 hr. The benzene solution was washed with 5% (w/v) sodium bicarbonate solution (2×20 ml), 0.1N HCl solution (2×20 ml) and with brine (2×20 ml). The organic layer was dried over anhydrous magnesium sulfate and concentrated under vacuum to get a crude yield of 2.178 g. This material was purified by passage through a silica gel column by eluting with 5% ethyl acetate in petroleum ether to give 953 mg (2.4 umol) of the pure compound (yield 69.5%). The characteristics of the thus obtained compound were as follows:

TLC: R$_F$ 0.66 ethyl acetate:pet ether (1:1)
IR (Neat): 1730 (C=0), 1370
NMR (DCDl$_3$): δ 5.35 (m, 6H, vinyl-H) 3.6-4.35 (m, 5H, glycerol CH$_2$, CH) 2.75, (m, 4H), 2.25 (1,J=8 Hz, 2H), 1.70-2.15 (m, 4H), 1.15-1.70 (bs, 16H), 0.95 (t,J=8 Hz, 3H)
Anal.: (C$_{24}$H$_{40}$O$_4$) C,H b) Using Linolenoyl chloride To a solution of 660 mg (5 mmol) of glycerol acetonide (20) and 620 mg (5 mmol) of 4-dimethylaminopyridine (DMAP) in 30 ml of dry benzene under N$_2$ atmosphere was added a solution of linolenoyl chloride (Eastman, freshly distilled) 1.49 g (5 mmol) in 20 ml benzene from a pressure equalizing funnel over 45 min. The DMAP hydrochloride was precipitated as a white solid during the reaction. The reaction mixture was treated as above, after stirring for another 2.5 hr. The crude product (2 g) was distilled to get 1.32 g of Compound 21 (yield 67%) (b.p. 155°-60° C./0.05 min).

Symmetrical t-BOC-GABA anhydride

The compound was prepared by reacting t-BOC-GABA or t-BOC ($^{14}$C)GABA with dicyclohexyl carbodiimide.

1-Glyceryl linolenoate (Compound 22)

A solution of 1.2 g (3.1 umol) of the linolenoyl ester of glycerol acetonide in 60 ml of dry methylene chloride was stirred with 2.2 ml of trifluoracetic acid at 0° C. for 12 h under N$_2$. The solution was concentrated in a rotary evaporator, and traces of the trifluoracetic acid were removed under high vacuum. The crude material was purified by chromatography on a silica gel column, eluting with ethyl acetate (yield 30%) in petroleum ether to obtain 730 mg (2.1 umol) (yield 68%). The product (Compound 22) migrated as a single spot on TLC plates and had NMR and IR spectra consistent with their proposed structure. This was used without further purification for the next step. The characteristics of this compound were:

TLC: R$_f$ 0.12 ethyl acetate:pet ether,
IR (Neat): 3500-3700, 1725
NMR ((CDCl$_3$): δ 5.25-5.46(m, 6H, CH=CH) 3.60-4.20(m, 5H, glycerol CH,CH$_2$) 2.68-2.80(m, 4H), 1.88-2.45(m, 6H) 1.31(bs, 12H), 0.97(t, J=9 Hz, 3H).

1-linolenoyl-3-(N-gamma-t-BOC aminobutyroyl) glycerol (Compound 23)

t-BOC-GABA anhydride (250 mg, 640 umol) and 4-dimethlyaminopyridine (80 mg, 660 umol) were added to a solution of 1-linolenoyl glycerol (470 mg, 1.34 mmol) in 50 ml of dry benzene. The mixture was stirred overnight under N$_2$ atmosphere. The benzene solution was then extracted with 0.1N HCl solution, 5% (w/v) aqueous NaHCO$_3$ and water. The organic layer was removed and dried over anhydrous MgSO$_4$ and concentrated in vacuo to yield 504 mg of crude product. This material (Compound 23) was then purified by chromatography in a silica gel column, eluting with 30% ethyl acetate in petroleum ether to yield 234 mg (440 umol) of a compound (TLC pure) as a viscous liquid (yield 68%). The characteristics of the compound were found to be as follows:

TLC: $R_f$ 0.45 ethyl acetate:pet ether, 1:1
IR (Neat): 3600, 1725, 1680
NMR (CDCl$_3$): δ 5.29-5.43 (m, 6H, vinyl-H) 4.15 (m, 5H glycerol CH,CH$_2$) 3.13-3.21 (m, 2H), 2.80 (m, 4H) 2.31-2.39 (m, 4H, 1.45-2.25 (m, 6H) 1.43 (s,9H), 1.25 (bs, 12 H) 0.97 (t(J-9 Hz), 3H)
Anal: (C$_{30}$H$_{51}$NO$_7$) C,H,N.

The same procedures were used on a microscale (20 mg) to synthesize the compound as a radioactive derivative using $^{14}$C-labeled t-BOC-GABA anhydride.

1-linolenoyl-2,3-di(N-gamma-t-BOC-aminobutyroyl) propane-1,2,3-triol (Compound 24)

The symmetrical anhydride of t-BOC GABA (567 mg, 1.45 mmol) and 4-dimethylaminopyridine, 178 mg (1.45 mmol) were added to a solution of 1-linolenoyl glyceride (256 mg, 730 umol) in 50 ml of dry benzene. The mixture was stirred for 6 hr under nitrogen atmosphere. The reaction product as a solution in benzene was extracted with the following, in sequence: 0.1N HCl (2×20 ml), 5% (w/v) NaHCO$_3$ solution (2×20 ml) and with brine (2×20 ml). The organic layer was separated and dried over anhydrous MgSO$_4$ and concentrated in vacuo to yield 1.23 g of the crude product (Compound 24). The material was then passed through a silica gel column. Elution with petroleum ether:ethyl acetate (80:20) yielded the pure product, 356 mg, 0.49 mmol (yield 68%). The characteristics of the compound are as follows:

TLC: $R_f$ 0.67 in ethyl acetate:pet ether, 1:1
IR (Neat): 3500, 1725, 1695
NMR (CDCl$_3$): δ 5.35 (bm, 6H, CH=CH) 3.95-4.75 (m, 5H glycerol-CH$_2$,CH) 3.1 (m, $\overline{4}$H), $\overline{2}$.75 (m,4H) 2.1-2.5 (bm, 6H), 1 $\overline{5}$-2.1 (m, 8H) 1.45 (s, 18H), 1.3 (bs, 12H) 0.97 (t,J=8 Hz, 3H)
Anal: (C$_{39}$H$_{66}$N$_2$O$_{10}$) C,H,N 1,2-dilinolenoyl-3-(N-gamma-t-BOC aminobutyroyl) propane-1,2,3-triol (Compound 25)

A solution of linolenoyl chloride (11 mg, 380 mol) in 10 ml of dry benzene was added dropwise from a pressure equalizing funnel to a solution of 1-linolenoyl-3-(N-gamma-t-BOC aminobutyroyl) glycerol (Compound 23) (193 mg, 361 umol) and 4-dimethylaminopyridine (55 mg, 0.47 mmol) in 15 ml of dry benzene at 0° C. under N$_2$. The mixture was stirred for 4 hr at about 10° C., after which the benzene solution was washed with 0.1N HCl, 5% (w/v) NaHCO$_3$ and finally saturated NaCl solution. The organic layer was separated, dried over anhydrous MgSO$_4$, and concentrated in vacuo to yield 223.7 mg of crude material. This was adsorbed onto a silica gel column and eluted with 15% ethyl acetate in petroleum ether to yield 186.4 mg (yield 65%) of the purified Compound 25.

TLC: $R_f$ 0.40 ethyl acetate:pet ether, 1:9
IR (Neat): 3450, 1730, 1710
NMR (CDCl$_3$): δ 5.36 (9H, m, vinly H) 4.21 (m, 5H glycerol CH,CH$_2$) 3.15 (m, 2H), 2.80 (m, 6H) 1.4-2.40 (m, 16H), 1.43 (s, 9H) 1.31-1.25 (bs, 20H), 0.97 (m,6H)
Anal (C$_{48}$H$_{70}$NO$_8$) C,H,N.

1-linolenoyl-2,3-(gamma-aminobutyroyl)propane-1,2,3-triol (Compound 26)

The 1-linolenoyl-2,3di(N-gamma-t-BOC aminobutyroyl ester) (Compound 24) (200 mg, 277 umol) in 50 ml of dry methylene chloride containing 2.2 ml of trifluoroacetic acid was stirred at 0° C. under N$_2$ for 6 hr. The solution was concentrated under vacuum and was taken up in 15 ml of ethyl acetate. The ethyl acetate solution was treated for 2 min with saturated NaCl solution adjusted to pH 8.5 with NaHCO$_3$. The organic layer was separated, dried over anhydrous Na$_2$SO$_4$ and concentrated under vacuum to obtain 98 mg (188 mol) of the diamine (Compound 26) (yield 68%). The other characteristics of the compound were as follows:

TLC: $R_f$ 0.77 in BuOH:AcOH:pyridine: water, 5:1:3:3:4 vols
IR (Neat): 3000-3500 (broad), 1720, 1680
NMR(CDCl$_3$): 7.95 (bm, 4H), 5.35 (m, 4H) 1.4-2.6 (m, 14H), 1.1-1.7 (m,10H) 0.06 (t(J=7H), 3H)

Since the free amine was unstable the di-N-acetyl derivative (27) was used for analysis, and it was obtained by acetylation with acetic anhydride in pyridine:
Anal. (C$_{33}$H$_{54}$N$_2$O$_8$) C,H,N.

The Compound 26 was synthesized by the above methods as a radioactive derivative on a microscale (20 mg). All the radioactivity in the compound was present as $^{14}$C in the GABA moiety of the compound. The product had a specific activity of 139 Ci/mmol and migrated with a $R_f$ 0.77 (BuOH, AcOH, pyridine, H$_2$O 5:1:3:3:4) on TLC plates.

1,2-dilinolenoyl-3-(gamma-aminobutyroyl) propane-1,2,3-triol

A solution of 1,2-dilinolenoyl-3-(N-gamma-t-BOC aminobutyroyl)propane-1,2,3-triol (Compound 25) (40 mg, 0.05 mmol) in 15 ml of methylene chloride containing 0.25 ml of trifluoroacetic acid at 0° C. was stirred overnight under N$_2$. The solution was then concentrated under vacuum. The viscous residue was passed through a silica gel (8 g) column, eluting first with ethyl acetate: petroleum ether (1:1 vols) and then with chloroform: methanol (80:20 vols). The ninhydrin positive (TLC) fractions of the chloroform/methanol eluents were combined and concentrated to obtain 62.1 mg of material. This was dissolved in 15 ml of chloroform and treated with 10 ml of NaHCO$_3$ solution containing sodium chloride. The chloroform layer was separated, dried over anhydrous Na$_2$SO$_4$ and concentrated to yield 29.5 mg (45 umol) (84%) of pure product (Compound 28). The characteristics of the product were as follows:

TLC: $R_f$ 0.58 in chloroform:methanol, 9:3 vols
IR (Neat): 3500, 1730, 1675
NMR (CDCl$_3$): 5.35 (m, 12H, vinyl H) 4.22 (m, 5H, glycerol H) 2.70 (M, 2H), 2.41-1.37 (bm, 14H) 1.25(bs, 12H), 0.87(t(J=7.5 Hz), 6H)

Since the free amine was not stable the N-acetyl derivative (Compound 29) was prepared for analysis by reacting the free amine with acetic anhydride and 4-dimethylaminopyridine.

Compound 29 was also synthesized as a radioactive derivative using the above methods on a microscale. The product had all its label as $^{14}$C in the GABA substituent of the molecule. It migrated at an $R_f$=0.58 in (CHCl$_3$, CH$_3$OH, 9:3) on TLC, and had a specific activity of 41 uCi/mmol.

1-(gamma-carbobenzoxyaminobutyroyloxy)2,3-0-isopropylidenedioxy propane (Compound 30)

Isopropylidene glycerol (Compound 20) (370 mg, 2.8 umol), gamma-carbobenzoxyamino-butyric acid anhydride (1.28 g, 2.8 umol) and 4-dimethylaminopyridine (360 mg, 3 mmol) were dissolved in 20 ml of dry benzene and the solution was stirred overnight at room temperature under anhydrous conditions. The solution was washed with 5% sodium bicarbonate solution, 0.1N HCl solution and water. The organic layer was dried over anhydrous MgSO₄ and concentrated in vacuum to yield 849 mg (2.4 umol) (yield 86%) of product (Compound 30). The characteristics of Compound 30 were as follows:

TLC: R$_f$0.57 ethyl acetate:hexane, 1:1
IR (Neat) 3350, 1710, 1700
NMR (CDCl₃): δ 7.38 (s, 5H, aromatic H) 5.14 (s, 2H, benzyl CH₂) 4.7–5.05 (bm, 1H, NH) 3.60–4.50 (m, 5H, glycerol CH,CH₂) 3.25 (m, 2H), 2.40 (t(J=11 Hz)2H) 1.86 (m, 2H), 1.45 (s, 3H), 1.38 (s, 3H) Anal: (C₁₈H₂₅NO₆) C,H,N.

1-(gamma-aminobutyroyl)propane-1,2,3-triol
(Compound 31)

A solution of the carbobenzoxyl derivative (Compound 30, 200 mg, 570 umol) and 10% palladium on charcoal (30 mg) in 10 ml of ethanol was stirred overnight under H₂. The solution was filtered to remove the catalyst and was concentrated under vacuum to obtain the product (Compound 31) as a viscous liquid (104 mg, 432 umol) (yield 76%) which had a single ninhydrin-positive spot on analytical thin-layer chromatography. The characteristics of the compound were as follows:

TLC: R$_f$0.35 in chloroform:methanol, 3:9
IR (Neat): 3500, 1720
NMR (CDCl₃) (acetate salt): 6.8 (bs 3H), 4.4–3.55 (m, 5H) 2.85 (t, 3H), 2.43 (m, 2H) 1.95 (s, 3H), 1.4 (s, 3H) 1.35 (s, 3H), 1.2 (m, 2H)

The product obtained after hydrogenolysis (150 mg, 690 umol) was taken up in 20 ml of methylene chloride, and 0.2 ml of trifluoroacetic acid was added and the mixture was stirred at room temperature for 3 hr. The solvent was removed under vacuum, and the residue was passed through a silica gel column, eluting with chloroform: methanol to obtain 77.7 mg (267 umol) of the trifluoroacetate (yield 39%). The characteristics of the compound were as follows:

TLC: R$_f$0.45 in BuOH: AcOH: H₂O, 4:1:1
IR (Neat): 3500, 1670
NMR (CD₃COCD₃): δ41–3.05 (mg, 7H), 2.53 (t(J=7 Hz, 2H) 2.15 (m, merges with acetone peak) 1.55–1.05 (m, 2H)

A radioactive derivative (specific activity 645 uCi/mM) was synthesized using the above procedures with CBZ-¹⁴C(U)-GABA anhydride.

The overall yields with which some of the final products were obtained, as well as the specific activities of the corresponding ¹⁴C compounds labeled in the GABA radical are shown in Table I, hereinbefore. The results of the elemental analysis of compounds 21, 23, 24, 25, 30, 27 and 29 are shown in Table II, hereinbefore.

Melting points were determined on a hot stage Fisher Jones apparatus and are uncorrected. IR spectra were recorded on a Perkin-Elmer Infracord Spectrophotometer and are reported in cm⁻¹. NMR spectra were recorded on a CFR 20 Spectrometer. Chemical shifts are reported in parts per million with tetramethylsilane as the internal reference. The multiplicities are expressed as follows: s=singlet, d=doublet, t=triplet, q=quartet, m=multiplet, b=broad. Elemental analyses were performed by the Midwest Microlab Ltd., Indianapolis, Ind., and were in agreement (within±0.4%) with the proposed structures. Thin-layer chromatography (TLC) was performed on 100-um-thick precoated silica gel chromatogram sheets (Eastman).

BIOLOGICAL STUDIES WITH COMPOUNDS OF EXAMPLE 3

Brain Uptake Studies

The capacity of some of the compounds of Example 3 to penetrate the blood-brain barrier of test mice was evaluated by measuring their brain penetration index (BPI). Table VI lists the results obtained. The BPI value for GABA is 1.0%. This is increased by 90-, 127-, and 3-fold, respectively, for Compounds 26, 28, and 31. Thus, there seems to exist no blood-brain barrier for the lipid derivatives. In fact, the uptake into brain for Compound 28 is higher than in liver, suggesting that there is a preferential accumulation into the CNS. Studies of the time course of uptake indicate that the brain continues to accumulate Compounds 26 and 28, even at 3 and 4 hr after the s.c. injection, while liver levels reach a maximum at 45–60 min, and then decrease. This pattern is presumably due to the slow secondary release of the highly insoluble molecules into the bloodstream from lipid tissue stores or late absorption from the site of injection. Due to the similarity of the test compounds to natural components of membrane lipids (especially Compound 28), it seems probable that the compounds may become associated with brain membrane lipid bilayers to provide a reservoir for release of GABA by hydrolysis by the esterases that may be present in the CSF and brain membrane. Thin-layer chromatographic (TLC) analysis of tissue homogenates showed that 60% of the original Compound 26 was pre sent in brain as the intact molecule at 4 hr after the injection, whereas the liver and kidney of the same animal had only 30% and 10% of the radioactivity present as 26. The remainder of the label associated with each tissue was present mainly as low molecular weight volatile products (probably acetic acid) in the liver and kidney.

TABLE VI

| UPTAKE OF LIPID ESTERS OF GABA | | | | | | |
|---|---|---|---|---|---|---|
| COMPOUND | NO. | DOSE (umol/kg) | TIME (min) | (BRAIN) (nmol/g) | (LIVER) (nmol/g) | BPI (%) |
| GABA (G) | | 270 | 5 | 1.03 | 104 | 1 ± .09 |
| glyceryl- | 31 | 270 | 5 | 4.8 ± 0.2 | 157 ± 12 | 3 ± 0.35 |
| GABA | | 270 | 15 | 14 | 112 | 12 |
| | | 270 | 30 | 16.4 | 91 | 18 |
| linolenyl- | 26 | 188 | 5 | 3.0 ± 0.2 | 3.3 ± 0.2 | 90 ± 13 |
| diGABA- | | 200 | 60 | 2.4 | 2.9 | 87 |
| glyceride | | 360 | 180 | 9.4 | 5.5 | 170 |
| di | 28 | 67 | 5 | 5.9 ± 0.4 | 4.7 ± 0.4 | 127 ± 8.3 |
| linolenoyl | | 20 | 60 | 1.4 | 3.1 | 44 |
| GABA- | | 170 | 60 | 6.0 | 8.8 | 68 |

TABLE VI-continued

| COMPOUND | NO. | DOSE (umol/kg) | TIME (min) | (BRAIN) (nmol/g) | (LIVER) (nmol/g) | BPI (%) |
|---|---|---|---|---|---|---|
| glyceride | | 60 | 240 | 7.1 | 18.3 | 39 |

BPI = Brain Penetration Index, as defined hereinbefore. Each compound was tested in Balb/c mice (20 ± 2 g), as a solution in 0.5 ml of 25% (v/v) of propylene glycol in water. All the 5-min BPI values are the means ± S.E.M. for three measurements.

Measurement of Brain Penetration Index

Each of the $^{14}C$-labeled Compounds 26, 28 and 30 were in 125 ul of the propylene glycol diluted with water up to 0.5 ml, and then injected subcutaneously into test Balb/c mice (20±2 g weight). After 5 min the animals were sacrificed and the brain and liver were removed, weighed and homogenized in 8 ml and 10 ml of brain protein solvent, respectively. Next 0.5 ml aliquots were mixed with 10 ml of Aquasol 2 (New England Nuclear Corp., Boston, Mass.) and counted in a Beckman liquid scintillation counter. The data for the label in each tissue were used to calculate the total quantity of the compound present in brain and liver per gram of tissue. The ratio of the amount in brain as a percent of that present in liver at 5 min was taken as the Brain Penetration Index (BPI). Measurements at longer uptake times were also obtained to evaluate the accumulation of the compounds in the brain. The results of these tests are shown in Table VI hereinbefore.

PHARMACOLOGICAL PROPERTIES

The pharmacological properties of the lipid esters of GABA were evaluated by two methods.

(1) GENERAL LOCOMOTOR ACTIVITY

The general locomotor activity of mice was measured in the Stolting activity monitor apparatus during 60 min after an intraperitoneal (i.p.) injection of a test compound. Dose-response curves were obtained, and the dose at which behavioral activity was reduced by 50% ($ED_{50}$) was taken as a measure of the effectiveness of each compound. GABA itself had no significant effect even at a dose of 9.7 mmol/kg (1g/kg) whereas Compounds 26 and 28 were active at a much lower dose ($ED_{50}=69$ and 43 umol/kg, respectively). The results are shown in Table VII.

TABLE VII

| PHARMACOLOGICAL TESTING OF LIPID ESTERS OF GABA | |
|---|---|
| COMPOUND | $ED_{50}$ (INJECTED DOSE) (umol/kg) |
| GABA | >9700 × 10$^{3a}$ (inactive) |
| 26 | 69 |
| 28 | 43 |
| 31 | inactive |

The $ED_{50}$ data were obtained from dose-response measurements using 8 animals per dose. The changes are the 60-min general motor activity values as compared to vehicle-injected and uninjected controls.
$^a$The value for GABA was obtained for a 10-min time span after the injection; no significant differences from controls were observed for a 60-min time span.

Figure 2:
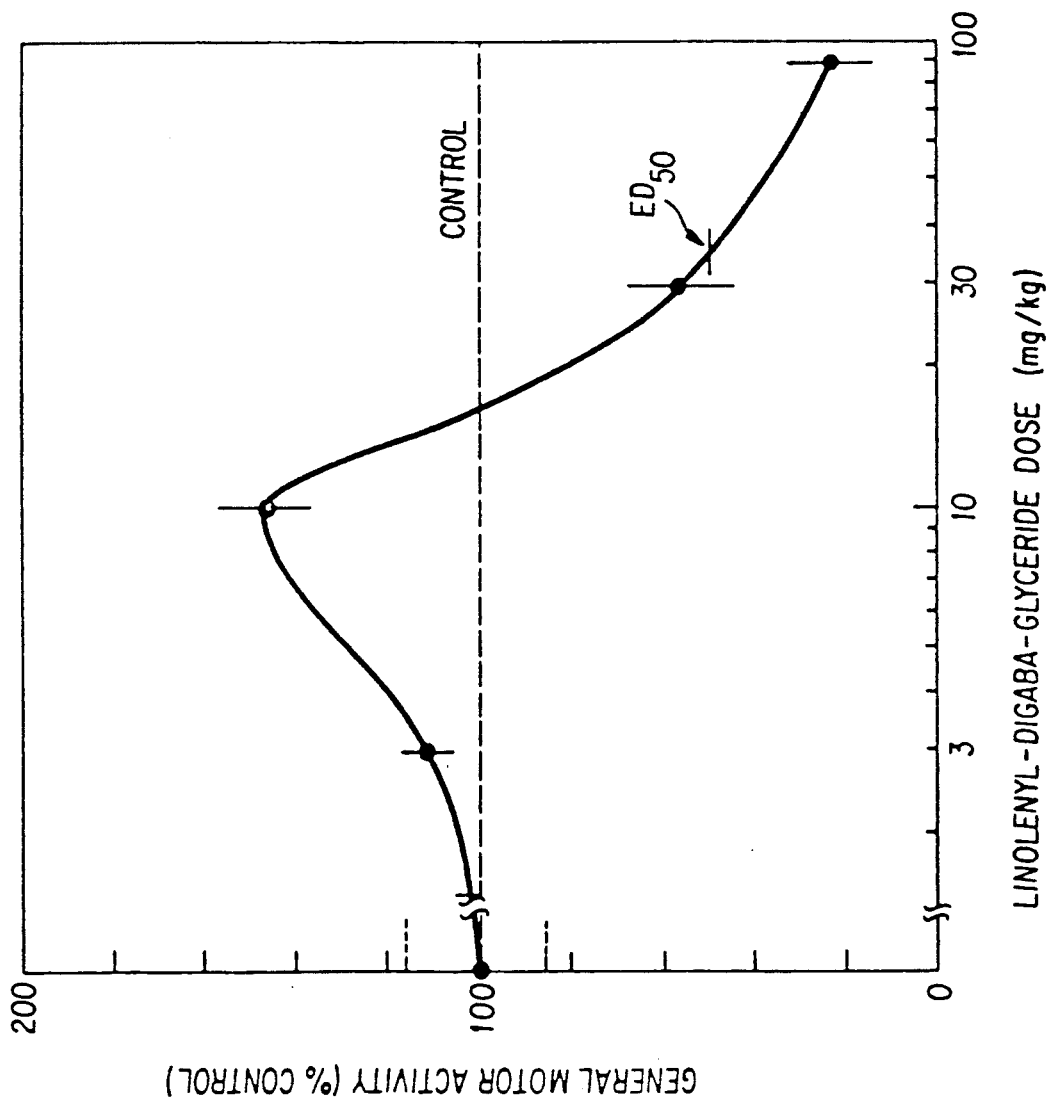
FIG. 2 shows the dose-response data for the effect of 1-linolenoyl-2,3-(4-aminobutyroyl) propane-1,2,3-triol (Compound 26) on the general motor activity of test mice. The compound enhances motor activity at the low dose of 10 mg/kg (19 umol/kg) and reduces activity at high doses ($ED_{50}$=36 mg/kg (69 umol/kg). The points show the mean±S.D. for eight test animals at each dose.

Measurements of the actual concentrations of the molecules present after 5 min in the brain at these doses by TLC indicated that 26 and 28 were present (at $ED_{50}$) at the level of 2.1 and 1.7 nmol, respectively per gram of brain tissue. The diGABA lipid analogue, Compound 26, also had the curious property of enhancing locomotor activity at doses below 10 mg/kg and depressing such behavior at high doses ($ED_{50}=36$ mg/kg) as is shown in FIG. 2. This result is similar to the reported effects of Baclofen (p-chlorophenyl GABA). The monoGABA ester of glycerol (Compound 31) was water soluble and showed insignificant pharmacological activity.

(2) Effect on bicuculline-induced seizures

The effect of the compound to delay the onset of a bicuculline-induced seizures was evaluated. Here, both Compounds 26 and 28 had only weak anticonvulsant properties when they were administered at doses of 30 mg/kg (50 umol/kg). These results suggest that the natural lipid esters of GABA have some sedative properties but lack substantial anticonvulsant effects.

(3) Effect on stereotypy behavior

Stereotypy tests were carried out by the method of A. Campbell et al., Neuropharmacol.: 21, 953 (1982). Test mice were pretreated with Compound 26 (i.p. injection), then 15 min later apomorphine or D-amphetamine sulfate was injected i.p. The animals were observed every 10 min and rated for stereotypic behavior in comparison to controls.

Rating scale:
0 = no stereotypy
1 = discontinuous sniffing
2 = continuous sniffing
3 = continuous sniffing and jaw movements The average total score per animal was obtained (maximum positive score = 18) over a 60-min period. A compound which depresses this score is considered to have properties of a neuroleptic with a potential for use as an antipsychotic agent. The results (see Table VIII) show a pronounced reduction of stereotypy, down to 24% of control.

TABLE VIII

| STEREOTYPY DATA | | |
|---|---|---|
| Induced By Dose | Apomorphine (1 mg/kg) | D-Amphetamine Sulfate (3 mg/kg) |
| Vehicle control | 15.3 ± 3 | 13.8 ± 1.5 |
| Compound 26 (170 umol/kg) | 8 ± 3.6 | 3.3 ± 0.9 |
| Stereotypy (% of control) | 52 | 24 |

Number of animals per test group = 4

EXAMPLE 4

Lipid/Water Distribution of Some Ester Derivatives of GABA

The lipid/water distribution of some of the compounds from Examples 2 and 3, as well as for GABA itself were determined by measuring the distribution of the compounds in a mixture of n-octanol and water.

Measurement of the n-Octanol/Water Partition Coefficient

The n-octanol/water partition coefficients were obtained from measurements of the distribution of 1, 3, 5 and 6 umol quantities of each $^{14}$C-labeled compound into a mixture of 5 ml of n-octanol and 5 ml water. At each concentration, the amount of labeled compound in the aqueous and n-octanol phases was calculated from the amount of radioactive material present after stirring for 18 hours. A plot of the amount in the n-octanol versus that in the aqueous phase gave a straight line with a slope of K, the partition coefficient.

$$K = \text{partition coefficient} = \frac{A \text{ n-octanol phase}}{A \text{ aqueous phase}}$$

where A the molar concentration of the compounds.

The data showing the lipid/water partition coefficients for the derivatives of GABA are shown in Table IX. Results from the experiments with the same ester derivatives of GABA described in Examples 1, 2 and 3 are also incorporated therein. The procedures followed for the determination of the effect of the compounds on the in vivo time of onset of bicuculline-induced seizures and on the in vivo inhibition of general locomotor activity are as described in the previous examples. The values for the brain penetration index (BPI) shown in Table I have also been incorporated into Table IX for comparative purposes.

TABLE IX

| LIPID/WATER PARTITION COEFFICIENTS | | | | |
|---|---|---|---|---|
| COMPOUND | BPI[f] | K[a]$_{OW}$ | In Vivo[b] | In Vivo[c,e] |
| GABA | 1 | 0.004 | 0 | 0 |
| Glyceryl-GABA | 3 | 0.01 | 0 | 0 |
| Inositol-tri GABA | 36 | n.d.[g] | n.d. | 4 |
| Dexamethasone-GABA | 81 | 0.9 | 0 | 0 |
| Inosital-GABA | 11 | n.d. | n.d. | 0 |
| 3-Glucosyl-GABA[d] | 104 | 0.21 | 0 | 0 |
| Butyl-GABA | 74 | n.d. | 1 | n.d. |
| Linolenoyl-GABA | 2 | n.d. | 0 | n.d. |
| diGABA-linolenoyl glyceride | 90 | 2.1 | 4 | 4 |
| GABA-dilinolenoyl glyceride | 127 | 6.6 | 5 | 4 |
| Cholesteryl-GABA | 25 | 110. | 5 | 5 |

[a]$K_{OW}$: Octanol/Water Partition Coefficient.
[b]In Vivo Delay of Time of Onset of Bicuculline-induced seizures.
[c]In Vivo Inhibition of General Motor Activity.
[d]The Hydroxyl group at position 1 is a mixture of the α and β isomers.
[e]1-5: active, with 5 most active 0: inactive
[f]BPI: Blood Penetration Index as defined hereinbefore.
[g]n.d.: not done The results of Table IX clearly distinguish between two groups of compounds. The first group is formed by compounds such as the cholesteryl ester of GABA which penetrate the blood-brain barrier and show biological activity in the present tests. The second group comprises compounds such as the glyceryl ester of GABA, which, although crossing the blood-brain barrier, do not show biological activity when administered at the indicated doses in the tests.

EXAMPLE 5

Pharmacological Studies with Compound 5 (Linolenoyl Ester of GABA) and Compound 6 (Cholesteryl Ester of GABA)

(1) Effect on bicuculine-induced seizures

The ability of a substance to delay the onset of bicuculline-induced epileptic seizures in the mouse was measured (Table X). There were no significant effects at 1 or 6 hr. At 24 hr after i.p. injection of the cholesteryl derivative (6) at a dose of 30 mg/kg (64 umol/kg), the onset of seizures was delayed by 30% (as compared to saline controls) after an acute i.p. injection of bicuculline at 0.3 mg/kg. In contrast, the linolenyl ester of GABA had the surprising property of accelerating the seizure onset time by 60% at a dose of 50 mg/kg, even though it had no significant effect on the general motor activity of mice. The dexamethasone and butyl esters had no effect on seizures in mice.

The fact that the bicuculline-induced seizures could be influenced at 24 hr after the administration of two GABA ester (5 and 6) but not at earlier times indicates that no significant direct, acute anticonvulsant activity can be ascribed to the compounds.

TABLE X

| ANTICONVULSANT PROPERTIES IN THE MOUSE | | | |
|---|---|---|---|
| Compound | Dose mg/kg | Onset of seizures: % Saline Control[a] | Survival Time: % Saline Control |
| saline | | 100 | 100 |
| vehicle | | 109 ± 7 | 123 ± 10 |
| cholesterol | 84 | 118 ± 6 | 110 ± 7 |
| 6 | 3 | 120 ± 6* | 95 ± 15 |
| 6 | 16 | 129 ± 4** | 101 ± 20 |
| 6 | 30 | 130 ± 8** | 104 ± 18 |
| 6 | 84 | 137 ± 7*** | 109 ± 9 |
| 5 | 12 | 102 ± 4 | 118 ± 10 |
| 5 | 17 | 73 ± 15** | 111 ± 14 |
| 5 | 25 | 78 ± 9** | 68 ± 9*** |
| 5 | 36 | 50 ± 5*** | 62 ± 6*** |
| 5 | 50 | 40 ± 11*** | 63 ± 8*** |

[a]Anticonvulsant action at 24 hr after pretreatment with the test compound. The seizure onset time was measured in seconds following an injection of bicuculline (0.3 mg/kg). Data for saline controls were 184 ± 19 and 253 ± 28 s, respectively, for onset of seizures and death with respect to 5. Data are means plus or minus SEM. n > 6 in each group.
* = $p < 0.5$;
** = $p < 0.05$;
*** = $p < 0.005$ by t test of difference between drug and saline controls.

(2) Measurement of activity of intact esters

The above results demonstrate that a compound such as cholesterol, which readily passes through the blood-brain barrier, can transport covalently bound GABA across the barrier. Once such a compound enters the CNS, its pharmacological activity could be due to the properties of the intact molecule or to its capacity to release GABA after hydrolysis. To test for the possibility that the intact molecules might be active, the capacity of Compounds 5 and 6 to inhibit the binding of [$^3$H]GABA to GABA "receptors" using membrane preparations of rat cerebellum were measured. IC$_{50}$, values were determined by fitting data to linearized transformations, based on including at least two concentrations of antagonists above and below the IC$_{50}$, with at least triplicate replication per concentration. The results (see Table XI) indicate that the concentrations of Compounds 5 and 6 required for 50% inhibition (IC$_{50}$) of binding were much greater than for GABA. Both Compounds 6 and 7 had low binding affinities to the receptors in comparison with potent GABA agonists, which can displace [$^3$H]GABA at low nanomolar concentrations. These results suggest that the pharmacological activity of the cholesteryl ester of GABA (6) is probably not due to its direct interactions at GABA-receptor binding sites; its activity might, however, be related to release of GABA by hydrolysis of the ester as a "prodrug".

TABLE XI

| INHIBITION OF [$^3$H]GABA BINDING TO SYNAPTIC MEMBRANES FROM RAT CEREBELLUM | |
|---|---|
| COMPOUND | IC$_{50}$,$^a$ nM |
| GABA | 70 |
| 5 | 40,000 |
| 6 | 10,000 |

$^a$The IC$_{50}$ value represents the dose of each compound required for 50% inhibition of the binding of [$^3$]GABA (15 nM) to synpatic membrane preparations (from rat cerebellum) in a receptor-binding assay.

(3) Enzymatic hydrolysis of cholesteryl [$^{14}$C] GABA ester by rat brain homogenate Cholesterol hydrolases and esterases are present in mammalian brain tissue. That such enzymes can release GABA from Compound 6 was demonstrated (see Table XII) with the crude supernatant (10,000 g, S$_1$) fraction of rat brain homogenates as a source of hydrolases.

TABLE XII

| ENZYMATIC HYDROLYSIS OF CHOLESTERYL [$^{14}$C]GABA ESTER BY RAT BRAIN HOMOGENATE | |
|---|---|
| Time/Min | Amount of Unreacted$^a$ Substrate (6), nmol |
| 10 | 53.0 ± 7.0 |
| 30 | 43.5 ± 6.3 |
| 60 | 34.5 ± 4.9 |
| Control$^b$ | 55.6 ± 2.6 |

$^a$Cholesteryl-[$^{14}$C]GABA ester (6) (3 mg/ml) was incubated at 37° C. in the presence of S$_1$ fractions of rat brain homogenates (0.8 mg/ml of protein). Analysis of 40 ul aliquots removed at various time intervals was carried out, after quenching the reaction with 0.5 ml of ethanol, by thin-layer chromatography (TLC) on silica gel in CHCL$_3$/MeOH/HOAc (18:6:1).
$^b$Control, the initial amount of substrate used, which did not change after 1 hr at 37° C.

(4) Inhibitory effect of cholesteryl GABA (C-G) Ester on evoked activity in rat hippocampal slices Cholesteryl gamma-aminobutyrate (C-G) produces a dose-dependent inhibition of orthodromically-evoked discharge of CA1 pyramidal cells. The duration of this inhibition is an order of magnitude longer than that produced by similar does of GABA. The inhibitory effect of C-G is antagonized by picrotoxin, by low chloride incubation medium, and by an esterase inhibitor. These observations are consistent with the notion that C-G has GABA-mimetic actions in the CNS, and that this property is dependent upon release of GABA from the compound by hydrolysis by esterases present in the tissue. Thus, C-G is a "prodrug" for delivery of GABA to the CNS.

Methods

Transverse slices of hippocampus (350-375 um thick) were prepared from Sprague-Dawley rats (200-300 g) and transferred onto a nylon net fixed over a 1.5 ml superfusion chamber. The slices were maintained at 32°-33° C. in a humidified atmosphere of 95%/5% O$_2$/CO$_2$. The standard medium consisted of (in mM): NaCl, 125; KCl, 3.5; CaCl$_2$, 2; MgS$_4$, 1.5; NaH$_2$PO$_4$, 1; NaHCO$_3$, 24; and glucose, 10. Low chloride medium was prepared by substituting sodium isethionate for sodium chloride.

Extracellular potentials were recorded with NaCl-filled micropipettes, and stimulus pulses were applied through bipolar platinum wire electrodes. The various drugs were dissolved in fresh medium (without glucose and phosphate) and applied to the surface of the tissue by pressure ejection from a micropipette, Sakai, Swartz and Woody, *Neuropharmacology:* 18.209-213 (1979).

The inhibitory effectiveness of various compounds was investigated by measuring their ability to suppress the extracellular population spike recorded from the hippocampal CA1 pyramidal layer and elicited by stimulation of stratum radiatum axons. The amplitude of this monosynaptic population spike is essentially proportional to the number of pyramidal cells discharging in response to a stimulus volley, Andersen, Bliss and Skrede, *Expl. Brain Res.:* 13, 208-221 (1971). These pyramidal cells are normally inhibited by GABA interneurons through a circuit which is largely recurrent and terminates extensively, but not exclusively, on the pyramidal cell bodies. Thus, application of compounds with GABA-like activity to the CA1 pyramidal layer mimisca normal inhibitory process tends to suppress pyramidal cell discharge, and reduces the amplitude of the evoked population spike, Alger, Jahr and Nicoll, *Adv. Biochem. Psychopharmac.:* 26, 77-91 (1981); Andersen, Dingledine, Gjerstad, Langmoen and Mosfeldt Laursen, *J. Physiol.:* 305, 279-296 (1980); Knowles and Schwartzkroin, *J. Neurosci.:* 1, 318-322 (1981); Schwartzkroin and Knowles, *Trends Neurosci.:* 6, 88-92 (1983).

The various compounds were applied as droplets to the pyramidal layer approximately 75 um from the recording electrode. The volume of a single drug application was about 300 picoliters. This droplet size was small enough to avoid any artifactual effects on the stimulating electrode, Langmoen, Segal and Andersen, *Brain Res.:* 208, 349-362 (1981). The volume ejected from each pipette was calibrated prior to use by measuring the diameter of the ejected droplet and adjusting the duration of the pressure pulse (usually 100-500 msec) until a standard diameter was reached. A constant droplet volume was used throughout the experiments. Where dose-response information was required, several pipettes with different drug concentrations were used. This method gave reproducible results, as indicated by the fact that different pipettes with the same drug concentration produced similar results.

Results

Droplets of GABA applied to the CA1 pyramidal layer produced rapid, dose-dependent inhibition of the evoked population spike. The maximum inhibitory effect was evident within a few seconds of droplet application, and recovery was usually complete within about 2-3 min. The effect could be repeated at 5- to 10-min intervals with little or no adaptation. Application of muscimol also produced dose-dependent inhibition of the CA1 population spike. The doses required (i.e., the concentration in the drug pipette) were nearly a thousand-fold lower than that of GABA for effects of comparable magnitude. In addition, the duration of the muscimol effect was roughly 100 times longer than that of a comparably effective dose of GABA.

In some experiments the extracellular synaptic potential was recorded from stratum radiatum, and the stimulation intensity was adjusted until no population spike was evoked. Under these conditions both GABA and muscimol applied to stratum pyramidale reduced the amplitude of this potential. This result is consistent with the large conductance increases in pyramidal cells associated with GABAergic synaptic action at the soma, Dingledine and Langmoen, *Brain Res.:* 185, 277–287 (1980), Alger et al., *Adv. Biochem. Psychopharmac.:* 26, 77–91 (1981), Andersen et al., *J. Physiol.:* 305, 279–296 (1980).

Addition of picrotoxin (10 uM) to the medium or replacement of the standard medium with low chloride medium significantly attenuates GABA-mediated inhibition in hippocampal slices, and a single stimulus pulse produces multiple population spikes, Ogata, *Expl. Neurol.:* 46, 147–155 (1975), Corrigall and Linseman, *Brain Res.:* 192, 227–238 (1980), Alger et al., *Adv. Biochem. Psychopharmac.:* 26, 77–91 (1981). Under these conditions, GABA and muscimol had little effect on the amplitude or number of evoked population spikes.

Application of cholestryl γ-aminobutyrate (C-G) to the CA1 pyramidal region of hippocampal slices also resulted in dose-dependent inhibition of the evoked population spike. The maximum magnitude of the C-G effect was less than that of a similar dose of GABA; however, the duration of the effect was roughly an order of magnitude longer. In the experiment, recovery of the population spike amplitude to 90% of the pre-droplet control value after an approximately half-maximal dose of C-G required about 14 min, while the recovery time after a GABA droplet was only 1–2 min.

Although C-G clearly produces a prolonged suppression of hippocampal pyramidal cell evoked discharge, the mechanism may be unrelated to GABA-mediated inhibition. If C-G acts by a GABAergic mechanism it should be antagonized by picrotoxin and by low chloride medium. Picrotoxin (10 uM) added to the medium did essentially eliminate the C-G effect. This antagonism was reversible; after washout of the picrotoxin, C-G was as effective as it was in the initial application. Replacing the standard medium with low chloride medium produced a similar result which was also reversed when standard medium was reintroduced. The results for the low chloride condition were obtained with C-G dissolved in low chloride medium. When C-G was dissolved in standard medium and applied to slices in low chloride medium, there was a small inhibitory effect which lasted no more than about a minute. This effect was presumably due to the chloride applied to the tissue along with the C-G. This observation emphasizes the chloride-dependent nature of the C-G inhibitory effect.

To test the possibility that the GABA-like actions of C-G are dependent on in situ enzymatic hydrolysis of the compound, experiments were conducted with phenylmethylsulfonylfluoride (PMSF) added to the slice incubation medium. PMSF is a potent, irreversible inhibitor of a variety of esterases, Gold, *Meth. Enzym.:* 11, 706–711 (1967), and in vitro experiments with brain homogenate show that PMSF significantly slows the degradation of C-G, Shashoua et al., *J. Med. Chem.:* 27, 659–664 (1984). Although PMSF is toxic, hippocampal slices can be incubated in 0.5 mm concentration for over 2 hr before showing significant loss of physiological activity, and if PMSF is removed after about 1 hr of incubation the slices appear to be physiologically stable for at least an additional 2 hr. When slices were incubated in PMSF (0.5 mM) for about 45 min, the inhibitory effect of C-G was significantly reduced. Washout of PMSF for about 1 hr did not reverse this effect. The effectiveness of GABA showed no change with PMSF, although recovery times seemed to be slowed somewhat. Thus, it appears that some esterase activity is essential to the physiological actions of C-G, but not to those of GABA.

All the compounds having an n-octanol/water partition coefficient greater than 0.9 were shown to be active both in the in vitro electrophysiological measurements of inhibitory effects on brain slices and in the in vivo inhibition of general motor activity. This type of result is consistent with the hypothesis that some lipid solubility must be present to allow the compounds to get into the cell membrane and interact with the GABA receptors.

EXAMPLE 6

Synthesis of Cholesteryl Gamma-Vinyl Gamma-Aminobutyrate Hydrochloride (Compound 33)

A. Cholesteryl gamma-vinyl-N-gamma-t-BOC-aminobutyrate (Compound 32)

A solution of cholesterol (80 mg, 0.206 mmoles), gamma-vinyl-N-t-BOC GABA (40 mg, 0.197 mmoles), dicyclohexyl carbodiimide (40 mg) and 4-dimethylaminopyridine (3 mg) in 20 ml of methylene chloride was stirred overnight at room temperature. The precipitated dicyclohexyl urea was removed by filtration.

The filtrate was washed with 0.1N HCl, 5% NaHCO$_3$ solution and brine. The organic layer was dried over Na$_2$SO$_4$ and concentrated, and the residue was purified by column chromatography over silica gel eluting with ethyl acetate and petroleum ether. Yield: 84 mg (75%) of Compound 32.

MP: 114°–115° C.

Analysis: Calc. for C$_{38}$H$_{63}$NO$_4$: C 76.38; H, 10.55; N, 2.35.

Found: C, 76,57; H, 10.12; N, 1.86.

IR (Nujol): 3360, 1725, 1690, 1175 cm$^{-1}$.

B. Cholesteryl gamma-vinyl gamma-aminobutyrate hydrochloride (Compound 33)

A solution of cholesteryl gamma-vinyl N-gamma-t-BOC aminobutyrate (Compound 32) (0.39 g, 0.65 mmoles) in 15 ml dioxane and 2 ml 4 m HCl-dioxane was stirred for 3 hr at room temperature. The product was precipitated as a white solid which was filtered and washed with ethyl acetate to get 244.5 mg (0.46 mmoles) of the hydrochloride.

IR (Nujol): 3500, 1725, 1605, 1510 cm$^{-1}$

EXAMPLE 7

Synthesis of Gamma-Vinyl GABA Glucose-3-Ester (Compound 35)

A. (1,2:5,6-diisopropylidene-D-glucose-3) gamma-vinyl N-gamma-t-BOC gamma-aminobutyrate (Compound 34)

A solution of 1,2:5,6-diisopropylidene-D-glucose (215 mg, 0.83 mmoles), gamma-vinyl-N-gamma-t-BOC amino butyric acid (gamma-vinyl BOC GABA) (166 mg, 0.73 mmoles), dicyclohexyl carbodiimide (170 mg) and 4-dimethylaminopyridine (12 mg) in 10 ml of methylene chloride was stirred at room temperature for 4 hr. The reaction mixture was filtered to remove dicyclohexyl urea (146 mg) that was precipitated during the reaction. The filtrate was concentrated to get 344 mg of crude product which was purified by passing through a small silica gel column with ethyl acetate and petroleum ether. Yield: 244 mg (71%) of Compound 34.

IR (Neat): 3450, 1730, 1690, 1640, 1510, 1360 cm$^{-1}$.

Analysis: Calc. for $C_{23}H_{37}NO_9$: C, 58.60, H, 7.86; N, 2.97.

Found: C, 58.53; H, 8.02; N, 2.80.

Gamma-vinyl GABA glucose-3-ester (Compound 35)

A mixture of (1,2:5,6-diacetone-D-glucose-3) gamma-vinyl-N-gamma-t-BOC aminobutyrate (Compound 3) (70 mg, 0.148 mmoles) in 4 ml of ethanol and 2N HCl (8 ml) was stirred overnight initially for 5 hr at room temperature and then at 5° C. The mixture was concentrated. The residue was taken in water and was filtered. This was concentrated and co-evaporated with ethanol to remove final traces of water. Yield: 45 mg (0.13 mmoles, 88%) of Compound 35.

TLC: $R_f$ 0.28 (propanol, acetic acid, water 8:1:1) (silica gel)

IR (Neat): 3400, 1725, 1625 cm$^{-1}$.

EXAMPLE 8

Synthesis of 1-Linolenoyl 2,3-Di(Gamma-vinyl-Gamma-Amino Butyryl) Glycerol, Dihydrochloride (Compound 37)

A. 1-Linolenoyl 2,3-di(gamma-vinyl-N-gamma-t-BOC aminobutyryl) glycerol (Compound 36)

A solution of linolenoyl glycerol (31 mg), gamma-vinyl BOC GABA (71 mg), dicyclohexyl carbodiimide (36 mg) and 4-dimethylaminopyridine (18 mg) in 10 ml of methylene chloride was stirred overnight at room temperature under nitrogen atmosphere. The mixture was filtered and the filtrate was washed with 0.1N HCl, 5% NaHCO$_3$ solution and brine. The organic layer was dried over anhydrous sodium sulfate and was concentrated to get a residue. This was purified by column chromatography on silica gel eluting with ethyl acetate and petroleum ether, to yield 53 mg of the product, Compound 36.

1-Linolenoyl 2,3-di(gamma-vinyl gamma-aminobutyryl) glycerol, dihydrochloride (Compound 37)

A solution of the di-BOC derivative (Compound 36) (16 mg) and 0.2 ml of HCl in dioxane (3M) in 3 ml of methylene chloride was stirred under nitrogen atmosphere at room temperature for 3-4 hr. The product was purified by column chromatography on silica gel using chloroform and methanol. Yield: 12.6 mg of Compound 37.

EXAMPLE 9

Synthesis 1-Linolenoyl-2N-Gamma-t-BOC Aminobutyryl 3-Gamma-Vinyl Gamma-Aminobutyryl Glycerol (Compound 40)

A. 1-Linolenoyl 2gamma-vinyl-N-gamma-t-BOC aminobutyryl glycerol (Compound 38)

A solution of monolinolenoyl glycerol, 31 mg (0.088 mmoles), gamma-vinyl BOC GABA, 18 mg (0.079 moles), dicyclohexyl carbodiimide, 18 mg and 4-dimethylaminopyridine, 3 mg, in 5 ml of methylene chloride was stirred overnight at room temperature under nitrogen atmosphere. The reaction mixture was filtered and the filtrate was washed with 0.1N HCl (ice cold), 5% sodium bicarbonate solution and brine. The solution was dried (Na$_2$SO$_4$) and concentrated to get 47 mg (0.087 mmoles, 99%) of crude product which was purified by column chromatography on silica gel, eluting with ethyl acetate, petroleum ether, Compound 38.

TLC: $R_f$ 0.6 (ethyl acetate, petroleum ether 1:1) (silica gel).

Analysis: Calc. for $C_{41}H_{68}N_2O_{10}$: C, 65.78; H, 9.09; N, 3.74.

Found: C, 65.82; H, 9.80; N, 3.99.

B. 1-Linolenoyl 2-N-gamma-t-BOC-aminobutyryl 3-N-gamma-t-BOC aminobutyryl glycerol (Compound 39)

A solution of the glycerol diester, 89 mg (0.166 mmoles), BOC-GABA anhydride, 90 mg and 4-dimethylaminopyridine, 22 mg, in 20 ml of benzene was stirred overnight at room temperature under nitrogen atmosphere. The mixture was worked up as before to get 115 mg (0.159 moles) of product. Yield 96%.

TLC: $R_f$ 0.6 (ethyl acetate, petroleum ether 1:1) (silica gel).

Analysis: Calc. for $C_{41}H_{68}N_2O_{10}$: C, 65.78; H, 9.09; N, 3.74.

Found: C, 65.82; H, 9.80; N, 3.99.

C. 1-Linolenoyl 2-gamma-aminobutyryl 3-gamma-vinyl-gamma-aminobutyryl glycerol dihydrochloride (Compound 40)

A solution of the di-BOC-amino derivative (28 mg and 4N HCl in dioxane (0.3 ml) in methylene chloride (4 ml) was stirred at room temperature for 3 hr. The mixture was concentrated in vaccum and the residue was purified on a silica gel column eluting with chloroform, methanol to yield 9 mg of the dihydrochloride, Compound 40.

TLC: $R_f$ 0.45 (chloroform, methanol, acetic acid 9:3:0.5) (silica gel).

EXAMPLES 10-19

The cholesteryl esters of gamma-methyl-GABA, gamma-hydroxymethyl-GABA, gamma-propargyl-GABA, gamma-phenanthryl-GABA, gamma-hydroxy-GABA, gamma-phenyl-GABA, gamma-(1-chlorophenyl)-GABA, beta-oxo-GABA, alpha-propoxy-GABA and N-acetyl-GABA are prepared in accordance with Example 6, producing Compounds 41 through 50, respectively.

EXAMPLES 20-29

The glucose-3 esters of beta-butyl-GABA, beta-hydroxy-methyl-GABA, beta-acetynyl-GABA, beta-hydroxy-GABA, gamma-phenyl-GABA, gamma-(1-methoxyphenyl)-GABA, beta-oxo-GABA, alpha-propoxy-GABA, N-pivalyl-GABA and N-pivalyl-alpha-methoxy-GABA are prepared according to Example 7, producing Compounds 51 to 60, respectively.

EXAMPLES 30-39

The 1-linolenoyl-2,3-diGABA analogue triesters of glycerol, where the GABA analogues are respectively gamma-methyl-GABA, beta-methoxy-GABA, alpha-methoxy-beta-methoxy-GABA, alpha-(3-hydroxyphenyl)-GABA, gamma-methyl-vinyl-GABA, gamma-i-propyl-GABA, gamma-fluoromethyl-GABA, gamma-difluoro-methyl GABA, beta-anthracyl-GABA and N-acetyl-GABA are prepared in a manner similar to Example 8, producing Compounds 61 to 70, respectively.

EXAMPLE 40

Self-Stimulation Reward Test

The procedure measured the capacity of a given pharmacological agent to inhibit rats from receiving stimulating currents provided by electrodes implanted in their brains (lateral hypothalamus), Stellar et al., *Pharmacol. Biochem. & Behav.:* 18, 433–442 (1983). The animals will press a lever to receive a current from the implanted electrode in preference to all else. The rate at which they press the lever depends on the intensity of the current (reward) that is being produced by the electrode. The intensity of the current is varied by raising the frequency at which 250 A pulses (0.1 msec duration) are delivered during a 0.5 sec time span in response to a lever press. A plot of the log of the frequency of the delivered pulses vs. the rate of lever presses for an animal gives a self-stimulation reward curve. Injection of a drug which has a tranquilizing effect shifts such a curve to higher frequencies. The shift of this curve (measured at the half-way point) gives a parameter which is expressed as the "Depression of the Self-Stimulation Reward" or DSSR. The maximum DSSR value obtained for the most powerful neuroleptics and tranquilizing compounds tested so far, seldom exceeds 0.3. This is designated as 100%. In the actual tests, the maximum DSSR value obtained for a given dose of drug and the half-life time [duration half-life (DHL)] of its return to 0% (the control state) was measured.

| Results of Self-Stimulation Reward Tests | | | |
|---|---|---|---|
| Compound | Dose (um/kg) | Max. DSSR | DHL |
| I (LGVG)* | 16 | 90 | 30 min |
| II (CVG)** | 40 | 83 | 24–48 hr |
| gamma-vinyl GABA (control) | 31 | 0 | 0 |

*linolenoyl gamma-aminobutyryl gamma-vinyl gamma-aminobutyryl glycerol
**cholesteryl gamma-vinyl gamma-aminobutyrate

EXAMPLE 41

Additional Self-Stimulation Reward Test

The procedure of Example 40 was repeated using the 1-linolenoyl-2,3 diGABA ester of glycerol ($LG_2$), the 1-linolenoyl-2,3-digamma-vinyl GABA ($LV_2$), the 1-linolenoyl-2-GABA,3-gamma vinyl GABA (LGV), the cholesteryl gamma-vinyl GABA (CV) and the valproyl GABA (ValG). The results are reported in the table below.

| Results of Additional Self-Stimulation Reward Test | | | |
|---|---|---|---|
| Compound | Dose (mg/kg) | DSSR (%) | DHL (min) |
| $LG_2$ | 26 | 100 | 70 |
| $LG_2$ | 13 | 100 | 65 |
| $LV_2$ | 13 | 100 | 65 |
| LGV | 24 | 100 | 65 |
| ValG | 20 | 0 | 0 |

Having now fully described this invention, it will be appreciated by those of ordinary skill in the art that the same can be practiced with a wide and equivalent range of compositions, modes of administration, therapeutic treatments, and the like, without affecting the spirit or scope of the invention or any embodiment thereof.

What is claimed is:

1. A compound of the formula:

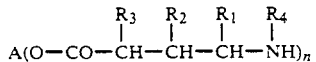

wherein:
$R_1$, $R_2$, and $R_3$ are the same or different and are selected from:
(a) hydrogen;
(b) lower alkyl groups having one to four carbon atoms;
(c) substituted lower alkyl group shaving one to four carbon atoms;
(d) lower alkenyl groups having one to four carbon atoms;
(e) substituted lower alkenyl groups having one to four carbon atoms;
(f) lower alkynyl groups having one to four carbon atoms;
(g) substituted lower alkynyl groups having one to four carbon atoms;
(h) aryl groups;
(i) substituted aryl groups;
(i) substituted aryl groups;
(j) hydroxyl groups or hydroxy groups protected with lower acyl or aroyl groups;
(k) lower acyl groups;
(l) oxo groups, in which case hydrogen is not present on the carbon atom;
(m) amino groups;
(n) substituted amino groups;
(o) $R_1$ and $R_3$ together forming a carbocyclic ring;
(p) $R_2$ and $R_3$ together forming a carbocyclic ring;
$R_4$ is hydrogen or acyl;
n can vary from 1 to the total number of esterifiable OH groups contained in A;
or pharmaceutically acceptable acid addition salts thereof,
said ester having a Brain Penetration Index greater than 2%.

2. The compound of claim 1 wherein $R_1$, $R_2$, and $R_3$ are each hydrogen.

3. The compound of claim 1, having a Brain Penetration Index greater than 3%.

4. The compound of claim 3 having a Brain Penetration Index greater than 25%.

5. The compound of claim 1, having an n-octanol/water partition coefficient greater than 0.5.

6. The compound of claim 1, wherein A represents the radical of a branched or unbranched saturated aliphatic alcohol having more than one OH substituent and a carbon chain of 2 to 40 carbon atoms.

7. The compound of claim 6, wherein the alcohol has the formula:

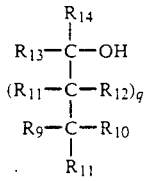

wherein:
(1) q is 1 to 38;
(2) $R_9$, $R_{10}$, $R_{11}$, $R_{12}$, $R_{13}$ and $R_{14}$ may be the same or different, and represent:
(a) H, with the proviso that at least one is different from H;
(b) OH, except that $R_{13}$ and $R_{14}$ cannot be OH;
(c) branched or unbranched amine of the formula $(CH_2)_nNH_2$, wherein n is 1 to 15;
(d) branched or unbranched alkyl of 1 to 15 carbon atoms;
(e) branched or unbranched hydrazino of the formula $(CH_2)_nNH-NH_2$, wherein n is as defined above;
(f) branched or unbranched haloalkyl of the formula $(CH_2)_nCX_mH_{(3-m)}$, wherein X represents F, Cl, Br., or I, n is as defined above, and m is 1 to 3;
(g) branched or unbranched alkenyl of 1 to 15 carbon atoms;
(h) branched or unbranched alkynyl of 1 to 15 carbon atoms;
(i) acetyl;
(j) their O-acetyl derivatives; and
(k) their O-methyl derivatives.

8. The compound of claim 7, wherein the alcohol has one or more carbon rings, and $R_{10}$ and $R_{12}$ may be a cyclic structure containing one or more carbon rings.

9. The compound of claim 8, wherein one or more of the carbon rings in the cyclic alcohol are aromatic.

10. The compound of claim 9, wherein the aromatic alcohol is a polyalcohol.

11. The compound of claim 1, wherein A represents the radical of a branched or unbranched aliphatic alcohol, having at least one point of unsaturation.

12. The compound of claim 11, wherein the alcohol is an alkenyl.

13. The compound of claim 11, wherein the carbon chain contains 3 to 40 carbon atoms.

14. The compound of claim 13, wherein the alcohol is an alkynyl.

15. The compound of claim 13, wherein the carbon chain contains 4 to 30 carbon atoms.

16. The compound of claim 15, wherein the carbon chain contains 8 to 20 carbon atoms.

17. The compound of claim 1, wherein A represents a radical of a branched or unbranched, saturated or unsaturated cyclic alcohol, having a maximum of 18 ring carbon atoms.

18. The compound of claim 17 having 5 to 14 carbon ring atoms.

19. The compound of claim 17 having 6 to 10 carbon ring atoms.

20. The compound of claim 17, wherein the cyclic alcohol is selected from the group consisting of cyclopentanol; cyclohexanol, cycloheptanol; cyclooctanol; cyclodecanol; cyclododecanol; cyclotetradecanol; cyclohexadecanol; cyclooctadecanol; inositol; their derivatives having multiple hydroxyl substituents; their O-acetyl derivatives; their O-methyl derivatives; their amine derivatives; and their halogenated derivatives.

21. The compound of claim 17, wherein the cyclic alcohol may contain one or more aromatic rings.

22. The compound of claim 1, wherein A represents the radical of a branched or unbranched alcohol with 2 to 40 carbon atoms having one or more non-heterocyclic heteroatoms.

23. The compound of claim 22, wherein A contains from 1 to 3 atoms of oxygen, nitrogen or sulfur, or a combination thereof.

24. The compound of claim 23, wherein the alcohol is a cyclic alcohol of 5 to 18 carbon ring atoms.

25. The compound of claim 24, having 6 to 10 carbon ring atoms.

26. The compound of claim 23, wherein A is selected from the group of alkyl, alkenyl and alkynyl alcohols having a carbon chain of 2 to 60 carbon atoms.

27. The compound of claim 26, wherein the alcohol has one or more aromatic rings.

28. The compound of claim 26, wherein the hetero alcohol is selected from the group consisting of ethanolamine, choline, serine, O-aminoacylglycerol, their alkyl derivatives, and their O-acyl derivatives.

29. The compound of claim 1, wherein A represents the radical of a glycerol esterified with up to two radicals of carboxylic acids having $C_2$-$C_{60}$ carbon atoms, which may be the same or different.

30. The compound of claim 29, wherein the carboxylic acids contain at least one point of unsaturation.

31. The compound of claim 30, wherein the carboxylic acids are derived from an alkenyl or alkynyl radical having more than one point of unsaturation.

32. The compound of claim 29, wherein the carboxylic acids, are branched or unbranched aliphatic acids having 6 to 40 chain carbon atoms.

33. The compound of claim 32 having 10 to 30 chain carbon atoms.

34. The compound of claim 32 wherein the carboxylic acids have an even number of carbon atoms.

35. The compound of claim 34, wherein the carboxylic acids are selected from a group consisting of tartaric acid, acetic acid, ascorbic acid, lauric acid, myristic acid, palmitic acid, stearic acid, arachidic acid, palmitoleic acid, oleic acid, linoleic acid, linolenic acid, arachidonic acid, cerebronic acid, cardiolyoin, their O-acetyl derivatives, their O-methyl derivatives, and their amino derivatives.

36. The compound of claim 29, wherein the glycerol radical is esterified by one fatty acid and one GABA or GABA analogue.

37. The compound of claim 29, wherein the glycerol radical is esterified by one fatty acid and two GABAs or two GABA analogues.

38. The compound of claim 29, wherein the glycerol radical is esterified by two fatty acids and one GABA or GABA analogue.

39. The compound of claim 1, wherein A is the radical derived form a compound selected from the group consisting of inositol, dilinolenoyl glycerol, and linolenoyl glycerol.

40. The compound of claim 1 wherein $R_2$, $R_3$ and $R_4$ are hydrogen, and $R_1$ is vinyl.

41. The compound of claim 1 which is gamma-vinyl GABA-di-linolenoyl-glyceryl triester.

42. The compound of claim 1 which is di-(gamma-vinyl GABA)-linolenoyl-glyceryl triester.

43. The compound of claim 1 wherein A represents the radical of dihydroxy acetone.

44. The compound of claim 1, wherein said compound is 1-linolenoyl-2,3-(gamma-aminobutyroyl)propane-1,2,3-triol.

45. The compound of claim 1, wherein said compound is 1,2-dilinolenoyl-3-(gamma-aminobutyroyl)-propane-1,2,3-triol.

46. The compound of claim 1, wherein said compound is 1-linolenoyl-2,3-(gamma-vinyl-gamma-aminobutyroyl)propane-1,2,3-triol.

47. The compound of claim 1, wherein said compound is 1-linolenoyl-2-(gamma-aminobutyroyl)-3-(gamma-vinyl-gamma-aminobutyroyl)propane-1,2,3-triol.

48. A pharmaceutical composition useful for promoting the brain uptake of a GABA- or GABA analogue-containing compound, comprising:

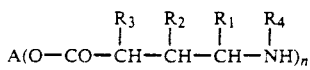

wherein:
$R_1$, $R_2$, and $R_3$ are the same or different and are selected from:
(a) hydrogen;
(b) lower alkyl groups having one to four carbon atoms;
(c) substituted lower alkyl groups having one to four carbon atoms;
(d) lower alkenyl groups having one to four carbon atoms;
(e) substituted lower alkenyl groups having one to four carbon atoms;
(f) lower alkynyl groups having one to four carbon atoms;
(g) substituted lower alkynyl groups having one to four carbon atoms;
(h) aryl groups;
(i) substituted aryl groups;
(j) hydroxy groups or hydroxy groups protected with lower acyl or aroyl groups;
(i) lower acyl groups;
(l) oxo groups, in which case hydrogen is not present on the carbon atoms;
(m) amino groups;
(n) substituted amino groups;
(o) $R_1$ and $R_3$ together forming a carbocyclic ring;
(p) $R_2$ and $R_3$ together forming a carbocyclic ring;
$R_4$ is hydrogen or acyl;
A represents the radical of a compound having at least one esterifiable OH group, selected from the group consisting of saturated Aliphatic alcohols having more than one OH substituent, unsaturated aliphatic alcohols, cyclic alcohols having 5 to 14 carbon ring atoms, aromatic alcohols, carbohydrates, alcohols containing at least one non-cyclic heteroatom and glyceryl esters of fatty acids; with the proviso that said alcohols are other than glycerol and are capable of crossing the blood-brain barrier of an animal;
n can vary from 1 to the total number of esterifiable OH groups contained in A;
or pharmaceutically acceptable acid addition salts thereof;
said ester having a Brain Penetration Index greater than 2%; and
a pharmaceutically acceptable excipient.

49. The pharmaceutical composition of claim 48 wherein each of $R_1$, $R_2$, and $R_3$ is hydrogen.

50. The composition of claim 48, wherein the excipient is suitable for the oral administration of the compound.

51. The composition of claim 50, wherein said composition is in the form of dragees, tablets, syrups and ampules.

52. The composition of claim 51, in unitary dosage form.

53. The composition of claim 48, wherein the excipient is suitable for the rectal administration of the compound.

54. The composition of claim 53, wherein said composition is in the form of a suppository.

55. The composition of claim 54, in unitary dosage form.

56. The composition of claim 48, wherein the excipient is suitable for the subcutaneous, intramuscular or intravenous administration of the composition.

57. The composition of claim 56, in unitary dosage form.

58. The composition of claim 48, wherein the excipient is suitable for the topical application of the compound.

59. The composition of claim 58, wherein the composition is in the form of a pomade a gel.

60. The composition of claim 59, in unitary dosage form.

61. The pharmaceutical composition of claim 48, wherein said compound is 1-linolenoyl-2,3-(gamma-aminobutyroyl)propane-1,2,3-triol.

62. The pharmaceutical composition of claim 48, wherein said compound is 1,2-dilinolenoyl-3-(gamma-aminobutyroyl)propane-1,2,3-triol.

63. The pharmaceutical composition of claim 48, wherein said compound is 1-linolenoyl-2,3-(gamma-vinyl-gamma-aminobutyroyl)propane-1,2,3-triol.

64. The pharmaceutical composition of claim 48, wherein said compound is 1-linolenoyl-2-(gamma-aminobutyroyl)-3-(gamma-vinyl-gamma-aminobutyroyl)propane-1,2,3-triol.

65. A method of promoting the uptake of GABA by the brain, comprising administration to a patient in need of said uptake at least one compound of the formula:

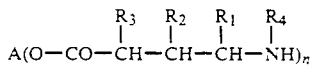

$R_1$, $R_2$, and $R_3$ are the same or different and are selected from:
(a) hydrogen;
(b) lower alkyl groups having one to four carbon atoms;
(c) substituted lower alkyl groups having one to four carbon atoms;
(d) lower alkenyl groups having one to four carbon atoms;
(e) substituted lower alkenyl groups having one to four carbon atoms;
(f) lower alkynyl groups having one to four carbon atoms;
(g) substituted lower alkynyl groups having one to four carbon atoms;
(h) aryl groups;
(i) substituted aryl groups;
(j) hydroxy groups or hydroxy groups protected with lower acyl or aroyl groups;
(k) lower acyl groups;
(l) oxo groups, in which case hydrogen is not present on the carbon atom;
(m) amino groups;

(n) substituted amino groups;
(o) $R_1$ and $R_3$ together forming a carbocyclic ring;
(p) $R_2$ and $R_3$ together forming a carbocyclic ring;
$R_4$ is hydrogen or acyl;

A represents the radical of a compound having at least one esterifiable OH group, selected from the group consisting or saturated Aliphatic alcohols having more than one OH substituent, unsaturated aliphatic alcohols, cyclic alcohols having 5 to 14 carbon ring atoms, aromatic alcohols, carbohydrates, alcohols containing at least one non-cyclic heteroatom and glyceryl esters of fatty acids; with the proviso that said alcohols are other than glycerol and are capable of crossing the blood-brain barrier of an animal;

n can vary from 1 to the total number of esterifiable OH groups contained in A;

or pharmaceutically acceptable acid addition salts thereof, said ester having a Brain Penetration Index greater than 2%, in an amount sufficient to promote the crossing of the blood-brain barrier of said patient by said compound.

66. The method of claim 65 wherein each of $R_1$, $R_2$, and $R_3$ is hydrogen.

67. The method according to claim 65, wherein said compound is 1-linolenoyl-2,3-(gamma-aminobutyroyl)-propane-1,2,3-triol.

68. The method according to claim 65, wherein said compound is 1,2-dilinolenoyl-3-(gamma-aminobutyroyl)propane-1,2,3-triol.

69. The method according to claim 65, wherein said compound is 1-linolenoyl-2,3-(gamma-vinyl-gamma-aminobutyroyl)propane-1,2,3-triol.

70. The method according to claim 65, wherein said compound is 1-linolenoyl-2-(gamma-aminobutyroyl)-3-(gamma-vinyl-gamma-aminobutyroyl)propane-1,2,3-triol.

71. A compound of the formula:

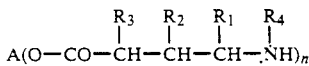

wherein:
$R_1$, $R_2$, and $R_3$ are the same or different and are selected from:
(a) hydrogen;
(b) lower alkyl groups having one to four carbon atoms;
(c) substituted lower alkyl groups having one to four carbon atoms;
(d) lower alkenyl groups having one to four carbon atoms;
(e) substituted lower alkenyl groups having one to four carbon atoms;
(f) lower alkynyl groups having one to four carbon atoms;
(g) substituted lower alkynyl groups having one to four carbon atoms;
(h) aryl groups;
(i) substituted aryl groups;
(j) hydroxy groups or hydroxy groups protected with lower acyl or aroyl groups;
(k) lower acyl groups;
(l) oxo groups, in which case hydrogen is not present on the carbon atom;
(m) amino groups;
(n) substituted amino groups;
(o) $R_1$ and $R_3$ together forming a carbocyclic ring;
(p) $R_2$ and $R_3$ together forming a carbocyclic ring;
$R_4$ is hydrogen or acyl;

A represents a glyceryl ester of a fatty acid capable of crossing the blood-brain barrier of an animal;

n can vary from 1 to the total number of esterifiable OH groups contained in A;

or pharmaceutically acceptable acid addition salts thereof, said ester having a Brain Penetration Index greater than 2%.

72. A pharmaceutical composition useful for promoting the brain uptake of a GABA- or GABA analogue-containing compound, comprising:

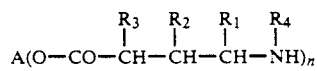

wherein:
$R_1$, $R_2$, and $R_3$ are the same or different and are selected from:
(a) hydrogen;
(b) lower alkyl groups having one to four carbon atoms;
(c) substituted lower alkyl groups having one to four carbon atoms;
(d) lower alkenyl groups having one to four carbon atoms;
(e) substituted lower alkenyl groups having one to four carbon atoms;
(f) lower alkynyl groups having one to four carbon atoms;
(g) substituted lower alkynyl groups having one to four carbon atoms;
(h) aryl groups;
(i) substituted aryl groups;
(j) hydroxy groups or hydroxy groups protected with lower acyl or aroyl groups;
(k) lower acyl groups;
(l) oxo groups, in which case hydrogen is not present on the carbon atom;
(m) amino groups;
(n) substituted amino groups;
(o) $R_1$ and $R_3$ together forming a carbocyclic ring;
(p) $R_2$ and $R_3$ together forming a carbocyclic ring;
$R_4$ is hydrogen or acyl;

A represents a glyceryl ester of a fatty acid capable of crossing the blood-brain barrier of an animal;

n can vary from 1 to the total number of esterifiable OH groups contained in A;

or pharmaceutically acceptable acid addition salts thereof, said ester having a Brain Penetration Index greater than 2%; and a pharmaceutically acceptable excipient.

73. A method of promoting the uptake of GABA by the brain, comprising administration to a patient in need of said uptake at least one compound of the formula:

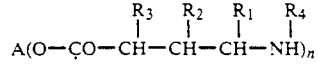

wherein:

$R_1$, $R_2$, and $R_3$ are the same or different and are selected from:
(a) hydrogen;
(b) lower alkyl groups having one to four carbon atoms;
(c) substituted lower alkyl groups having one to four carbon atoms;
(d) lower alkenyl groups having one to four carbon atoms;
(e) substituted lower alkenyl groups having one to four carbon atoms;
(f) lower alkynyl groups having one to four carbon atoms;
(g) substituted lower alkynyl groups having one to four carbon atoms;
(h) aryl groups;
(i) substituted aryl groups;
(j) hydroxy groups or hydroxy groups protected with lower acyl or aroyl groups;
(k) lower acyl groups;
(l) oxo groups, in which case hydrogen is not present on the carbon atom;
(m) amino groups;
(n) substituted amino groups;
(o) $R_1$ and $R_3$ together forming a carbocyclic ring;
(p) $R_2$ and $R_3$ together forming a carbocyclic ring;
$R_4$ is hydrogen or acyl;
A represents a glyceryl ester of a fatty acid capable of crossing the blood-brain barrier of an animal;
n can vary from 1 to the total number of esterifiable OH groups contained in A;
or pharmaceutically acceptable acid addition salts thereof,
said ester having a Brain Penetration Index greater than 2%,
in an amount sufficient to promote the crossing of the blood-brain barrier of said patient by said compound.

* * * * *